US012286646B2

(12) United States Patent
Irvine et al.

(10) Patent No.: US 12,286,646 B2
(45) Date of Patent: Apr. 29, 2025

(54) METHODS FOR IN VITRO EVOLUTION OF CONSTRUCTS DERIVED FROM VIRUSES

(71) Applicant: Massachusetts Institute of Technology, Cambridge, MA (US)

(72) Inventors: Darrell J. Irvine, Arlington, MA (US); Ron Weiss, Newton, MA (US); Yingzhong Li, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 928 days.

(21) Appl. No.: 16/739,182

(22) Filed: Jan. 10, 2020

(65) Prior Publication Data

US 2020/0224174 A1 Jul. 16, 2020

Related U.S. Application Data

(60) Provisional application No. 62/790,589, filed on Jan. 10, 2019.

(51) Int. Cl.

| | |
|---|---|
| ***C12N 7/00*** | (2006.01) |
| ***A61K 47/69*** | (2017.01) |
| ***A61K 49/00*** | (2006.01) |
| ***C12N 9/02*** | (2006.01) |
| ***C12N 15/10*** | (2006.01) |
| ***C12N 15/86*** | (2006.01) |

(52) U.S. Cl.

CPC ............ *C12N 7/00* (2013.01); *A61K 47/6929* (2017.08); *A61K 49/00* (2013.01); *C12N 9/0069* (2013.01); *C12N 15/1003* (2013.01); *C12N 15/1086* (2013.01); *C12N 15/1096* (2013.01); *C12N 15/86* (2013.01); *C12N 2770/36121* (2013.01); *C12N 2770/36143* (2013.01); *C12N 2770/36171* (2013.01)

(58) Field of Classification Search

None

See application file for complete search history.

(56) References Cited

U.S. PATENT DOCUMENTS

| | | | |
|---|---|---|---|
| 4,650,764 A | 3/1987 | Temin et al. | |
| 7,332,322 B2 | 2/2008 | Frolov et al. | |
| 2015/0159143 A1* | 6/2015 | Dowdy .................. | C12N 9/127 435/7.1 |

FOREIGN PATENT DOCUMENTS

| | | |
|---|---|---|
| WO | WO 2013/177133 A2 | 11/2013 |

OTHER PUBLICATIONS

GenBank Accession# DQ322642, VEEV replicon vector YFV-C3opt, complete sequence., Jan. 2006.*

Li et al., In vitro evolution of enhanced RNA replicons for immunotherapy. Sci Rep. May 6, 2019;9(1):6932. doi: 10.1038/s41598-019-43422-0. PMID: 31061426; PMCID: PMC6502795.

Li, Mutations from in vitro evolution affect existence of replicon RNA and transcription of subgenomic. 5th Intl Mammalian Synthetic Biology Workshop. 2018. Abstract.

Lundstrom, Replicon RNA Viral Vectors as Vaccines. Vaccines (Basel). Nov. 7, 2016;4(4):39. doi: 10.3390/vaccines4040039. PMID: 27827980; PMCID: PMC5192359.

Petrakova et al., Noncytopathic replication of Venezuelan equine encephalitis virus and eastern equine encephalitis virus replicons in Mammalian cells. J Virol. Jun. 2005;79(12):7597-608. doi: 10.1128/JVI.79.12.7597-7608.2005. PMID: 15919912; PMCID: PMC1143662.

Rose et al., In vitro evolution of high-titer, virus-like vesicles containing a single structural protein. Proc Natl Acad Sci U S A. Nov. 25, 2014;111(47):16866-71. doi: 10.1073/pnas.1414991111. Epub Nov. 10, 2014. PMID: 25385608; PMCID: PMC4250146.

Anderson et al., Nucleoside modifications in RNA limit activation of 2'-5'-oligoadenylate synthetase and increase resistance to cleavage by RNase L. Nucleic Acids Res. Nov. 2011;39(21):9329-38. doi: 10.1093/nar/gkr586. Epub Aug. 3, 2011.

Aznar et al., Intratumoral Delivery of Immunotherapy—Act Locally, Think Globally. J Immunol. Jan. 1, 2017;198(1):31-39.

Beal et al., Model-driven engineering of gene expression from RNA replicons. ACS Synth Biol. Jan. 16, 2015;4(1):48-56. doi: 10.1021/sb500173f. Epub Jun. 6, 2014.

Boyman et al., The role of interleukin-2 during homeostasis and activation of the immune system. Nat Rev Immunol. Feb. 17, 2012;12(3):180-90.

Davis et al., In vitro synthesis of infectious venezuelan equine encephalitis virus RNA from a cDNA clone: analysis of a viable deletion mutant. Virology. Jul. 1989;171(1):189-204.

Drake, Rates of spontaneous mutation among RNA viruses. Proc Natl Acad Sci U S A. May 1, 1993;90(9):4171-5.

Duportet et al., A platform for rapid prototyping of synthetic gene networks in mammalian cells. Nucleic Acids Res. Dec. 1, 2014;42(21):13440-51. doi: 10.1093/nar/gku1082. Epub Nov. 5, 2014.

Frolova et al., Roles of nonstructural protein nsP2 and Alpha/Beta interferons in determining the outcome of Sindbis virus infection. J Virol. Nov. 2002;76(22):11254-64.

Garmashova et al., Sindbis virus nonstructural protein nsP2 is cytotoxic and inhibits cellular transcription. J Virol. Jun. 2006;80(12):5686-96.

Gelderblom, Structure and classification of viruses. Chapter 41. Medical Microbiology. 4th Ed. 1996.

Guan et al., Nanotechnologies in delivery of mRNA therapeutics using nonviral vector-based delivery systems. Gene Ther. Mar. 2017;24(3):133-143. doi: 10.1038/gt.2017.5. Epub Jan. 17, 2017.

(Continued)

*Primary Examiner* — Benjamin P Blumel

(74) *Attorney, Agent, or Firm* — Wolf, Greenfield & Sacks, P.C.

(57) ABSTRACT

The disclosure provides methods for an in vitro evolution technique to identify and characterize mutations in the non-structural genes of an alphavirus replicon that increase the strength and persistence of expression of the replicon genome. Also provided herein are in vivo methods for administering to an animal model a mutated alphavirus replicon that codes for a gene of experimental or therapeutic interest in the subgenome of the alphavirus replicon. The mutations identified herein improve the therapeutic potential of self-replicating RNA, which may have implications for cancer immunotherapy and beyond, e.g., for vaccination or gene therapy.

20 Claims, 7 Drawing Sheets

Specification includes a Sequence Listing.

(56) References Cited

OTHER PUBLICATIONS

Guo et al., Effect of alpha interferon on the hepatitis C virus replicon. J Virol. Sep. 2001;75(18):8516-23.
Jensen et al., Sensing of RNA viruses: a review of innate immune receptors involved in recognizing RNA virus invasion. J Virol. Mar. 2012;86(6):2900-10. doi: 10.1128/JVI.05738-11. Epub Jan. 18, 2012.
Kaczmarek et al., Advances in the delivery of RNA therapeutics: from concept to clinical reality. Genome Med. Jun. 27, 2017;9(1):60.
Kariko et al., Incorporation of pseudouridine into mRNA yields superior nonimmunogenic vector with increased translational capacity and biological stability. Mol Ther. Nov. 2008;16(11):1833-40. doi: 10.1038/mt.2008.200. Epub Sep. 16, 2008.
Kawasaki et al., Recognition of nucleic acids by pattern-recognition receptors and its relevance in autoimmunity. Immunol Rev. Sep. 2011;243(1):61-73.
Kinney et al., Attenuation of Venezuelan equine encephalitis virus strain TC-83 is encoded by the 5'-noncoding region and the E2 envelope glycoprotein. J Virol. Mar. 1993;67(3):1269-77.
Kuhn et al., Phosphorothioate cap analogs increase stability and translational efficiency of RNA vaccines in immature dendritic cells and induce superior immune responses in vivo. Gene Ther. Aug. 2010;17(8):961-71. doi: 10.1038/gt.2010.52. Epub Apr. 22, 2010.
Kwong et al., Localized immunotherapy via liposome-anchored Anti-CD137 + IL-2 prevents lethal toxicity and elicits local and systemic antitumor immunity. Cancer Res. Mar. 1, 2013;73(5):1547-58. doi: 10.1158/0008-5472.CAN-12-3343. Epub Feb. 22, 2013.
Lächelt Nucleic Acid Therapeutics Using Polyplexes: A Journey of 50 Years (and Beyond). Chem Rev. Oct. 14, 2015;115(19):11043-78. doi: 10.1021/cr5006793. Epub Apr. 15, 2015.
Lastarza et al., Genetic analysis of the nsP3 region of Sindbis virus: evidence for roles in minus-strand and subgenomic RNA synthesis. J Virol. Sep. 1994;68(9):5781-91.
Li et al., Persistent Antigen and Prolonged AKT-mTORC1 Activation Underlie Memory CD8 T Cell Impairment in the Absence of CD4 T Cells. J Immunol. Aug. 15, 2015;195(4):1591-8. doi: 10.4049/jimmunol.1500451. Epub Jul. 10, 2015.
Lundstrom, Replicon RNA Viral Vectors as Vaccines. Vaccines (Basel). Nov. 7, 2016;4(4):39.
Macdonald et al., The zinc finger antiviral protein acts synergistically with an interferon-induced factor for maximal activity against alphaviruses. J Virol. Dec. 2007;81(24):13509-18. doi: 10.1128/JVI.00402-07. Epub Oct. 10, 2007.
Marabelle et al., Intratumoral immunization: a new paradigm for cancer therapy. Clin Cancer Res. Apr. 1, 2014;20(7):1747-56.
Mayuri et al., Role for conserved residues of sindbis virus nonstructural protein 2 methyltransferase-like domain in regulation of minus-strand synthesis and development of cytopathic infection. J Virol. Aug. 2008;82(15):7284-97. doi: 10.1128/JVI.00224-08. Epub May 21, 2008.
Merly et al., Murine RAW 264.7 cell line as an immune target: are we missing something? Immunopharmacol Immunotoxicol. Apr. 2017;39(2):55-58. doi: 10.1080/08923973.2017.1282511. Epub Feb. 2, 2017.
Naka et al., Interferon resistance of hepatitis C virus replicon-harbouring cells is caused by functional disruption of type I interferon receptors. J Gen Virol. Oct. 2005;86(Pt 10):2787-2792.
Pietschmann et al., Characterization of cell lines carrying self-replicating hepatitis C virus RNAs. J Virol. Feb. 2001;75(3):1252-64.
Prabakaran et al., Post-translational modification: nature's escape from genetic imprisonment and the basis for dynamic information encoding. Wiley Interdiscip Rev Syst Biol Med. Nov.-Dec. 2012;4(6):565-83. doi: 10.1002/wsbm.1185. Epub Aug. 15, 2012.
Puri et al., Lipid-based nanoparticles as pharmaceutical drug carriers: from concepts to clinic. Crit Rev Ther Drug Carrier Syst. 2009;26(6):523-80.
Ramaswamy et al., Systemic delivery of factor IX messenger RNA for protein replacement therapy. Proc Natl Acad Sci U S A. Mar. 7, 2017;114(10):E1941-E1950. doi: 10.1073/pnas.1619653114. Epub Feb. 15, 2017.
Rodriguez-Madoz et al., Semliki forest virus vectors engineered to express higher IL-12 levels induce efficient elimination of murine colon adenocarcinomas. Mol Ther. Jul. 2005;12(1):153-63.
Sanjuan et al., Viral mutation rates. J Virol. Oct. 2010;84(19):9733-48. doi: 10.1128/JVI.00694-10. Epub Jul. 21, 2010.
Schott et al., Viral and Synthetic RNA Vector Technologies and Applications. Mol Ther. Sep. 2016;24(9):1513-27. doi: 10.1038/mt.2016.143. Epub Jul. 5, 2016.
Shin et al., Structural and functional insights into alphavirus polyprotein processing and pathogenesis. Proc Natl Acad Sci U S A. Oct. 9, 2012;109(41):16534-9. doi: 10.1073/pnas.1210418109. Epub Sep. 25, 2012.
Stein et al., Sensing adenovirus infection: activation of interferon regulatory factor 3 in RAW 264.7 cells. J Virol. Apr. 2012;86(8):4527-37. doi: 10.1128/JVI.07071-11. Epub Feb. 15, 2012.
Strauss et al., The alphaviruses: gene expression, replication, and evolution. Microbiol Rev. Sep. 1994;58(3):491-562.
Van den Boorn et al., Turning tumors into vaccines: co-opting the innate immune system. Immunity. Jul. 25, 2013;39(1):27-37.
Wroblewska et al., Mammalian synthetic circuits with RNA binding proteins for RNA-only delivery. Nat Biotechnol. Aug. 2015;33(8):839-41. doi: 10.1038/nbt.3301. Epub Aug. 3, 2015.
Ying et al., Cancer therapy using a self-replicating RNA vaccine. Nat Med. Jul. 1999;5(7):823-7.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Yoshioka et al., Efficient generation of human iPSCs by a synthetic self-replicative RNA. Cell Stem Cell. Aug. 1, 2013;13(2):246-54.
Zavala-Cerna et al., The clinical significance of posttranslational modification of autoantigens. Clin Rev Allergy Immunol. Aug. 2014;47(1):73-90.
PCT/US2020/013004, Apr. 23, 2020, International Search Report and Written Opinion.
PCT/US2020/013004, Jul. 22, 2021, International Preliminary Report on Patentability.

* cited by examiner

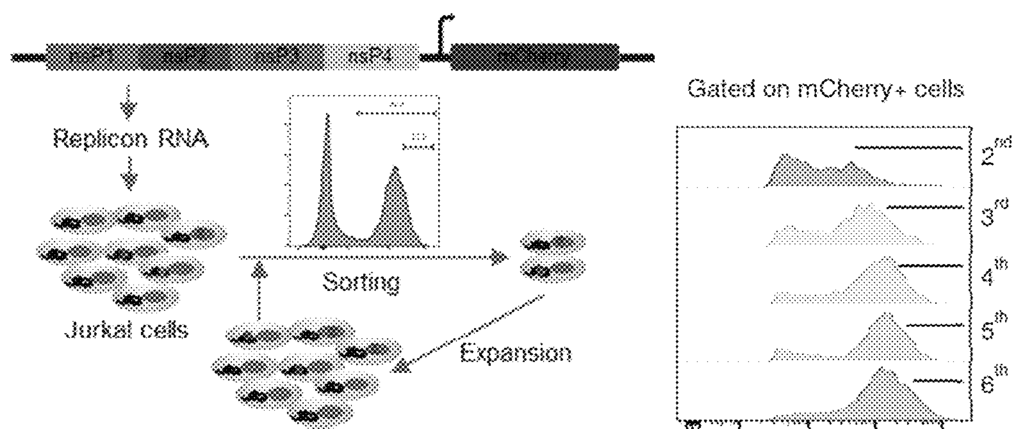
FIG. 1A
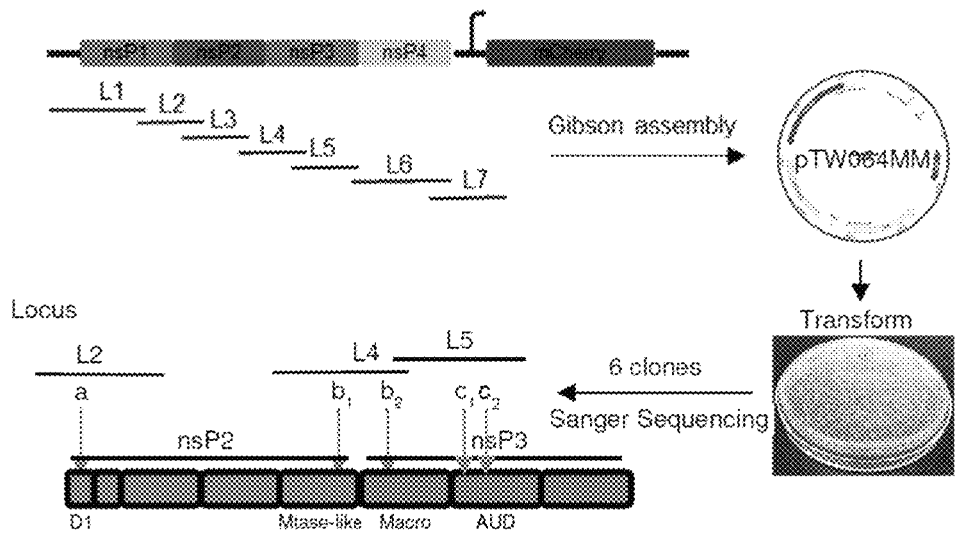
FIG. 1B
| Locus | Mutation rate | Nucleotide mutation | Amino acid mutation | Mutation region | Mutant allele |
|---|---|---|---|---|---|
| L2 | 16.7% | A1979G | G656G | nsP2 | a |
| L4 | 20% | G3936C | G1309R | nsP2 | $b_1$ |
| L4 | 40% | A4311G | K1434E | nsP3 | $b_2$ |
| L5 | 16.7% | A4758G | S1583G | nsP3 | $c_1$ |
| L5 | 16.7% | G4796T, G4944A | E1595D, V1645M | nsP3 | $c_2$ |
FIG. 1C

METHODS FOR IN VITRO EVOLUTION OF CONSTRUCTS DERIVED FROM VIRUSES

RELATED APPLICATION

This application claims priority under 35 U.S.C. § 119(e) to U.S. provisional patent application No. 62/790,589, filed Jan. 10, 2019, the entire contents of which are incorporated herein by reference

GOVERNMENT SUPPORT

This invention was made with Government support under Grant No. R01-CA206218 awarded by the National Institutes of Health. The Government has certain rights in the invention.

FIELD

Disclosed herein are methods for in vitro evolution to identify mutations in the non-structural proteins of synthetic alphavirus replicons and the role of the mutations in replicon duration and cargo gene expression. Also disclosed herein are methods for expressing a mutated alphavirus replicon in vivo in order to explore the expression of a detectable molecule or to explore its efficacy for expressing a subgenomic therapeutic gene.

BACKGROUND

Nucleic acid therapeutics have the potential to treat or cure many diseases that are difficult to address with more traditional therapies.[1] Delivery of exogenous nucleic acids to host cells allows therapeutic proteins to be produced that retain native conformations and post-translational modifications (e.g., glycosylation)[2,3] that are sometimes difficult to achieve with recombinant proteins. Synthetic mRNA in particular is attractive for its improved safety profile relative to viral or DNA-based modalities; the likelihood of genomic integration is low, and hence oncogenesis is less of a concern.[4] These advantages make synthetic mRNA an attractive platform for vaccines, cancer therapeutics, and therapies that compensate for (or correct) genetic defects, among others.[5]

Unfortunately, synthetic RNAs degrade rapidly in recipient cells, limiting their therapeutic utility. A synthetic RNA's persistence can be extended by biological modifications (such as enzymatic capping and polyadenylation) and incorporation of chemically modified nucleotides,[6-8] but even modified RNAs often remain active in cells for only several days,[9] making them unsuitable for long-term gene therapy. One alternative approach is to employ replicons derived from alphaviruses, positive-strand RNAs that encode RNA-dependent RNA polymerases which simultaneously translate therapeutic payloads and self-amplify the replicon on entry in to the cytoplasm.[10] Typically, therapeutic replicons are constructed by retaining the UTRs, non-structural proteins and subgenomic promoter (SGP) of the parent alphavirus, but the structural proteins in the subgenomic region are either fused with genes of experimental or therapeutic interest, or replaced with therapeutic genes and combined with helper constructs encoding structural proteins for making viral particles. Replicons delivered as non-replicating viral replicon particles or as synthetic RNA encapsulated in lipid nanoparticles have shown promise as vaccine vectors,

[11,12] for expression of therapeutic agents in cancer immunotherapy,[13,14] and for correction of genetic defects, such as hemophilia.[15]

SUMMARY

Motivated by these promising examples, strategies to regulate gene expression using replicons derived from the Venezuelan Equine Encephalitis (VEE) virus were explored herein.[16,17] Because replicons encode proteins necessary to copy the RNA itself, they persist in cells longer than modified synthetic RNA and can express genes in the subgenome at a high level. However, even though gene expression from the replicon is stronger and lasts longer than comparable synthetic mRNAs, expression still fades gradually[18] due to the host cell's innate immune response.[19-23]

Described herein is an in vitro evolution method to identify and characterize mutations in a synthetic alphavirus replicon. Also described herein are methods of engineering a mutated synthetic alphavirus replicon that includes one or more genes that encode a therapeutic agent, and administering the replicon to a subject. As shown herein, certain mutations in the synthetic alphavirus enhance replicon persistence and subgenomic expression of the therapeutic agent. The methods described herein show great potential for improving the replicon-based RNA therapeutics for vaccination, cancer immunotherapy, and gene therapy.

In some aspects, the disclosure provides methods for in vitro evolution of alphavirus replicons. The methods include engineering and synthesizing a synthetic replicon construct, transfecting the synthesized replicon RNA into cells with interferon responses, culturing the transfected cells for a first predetermined length of time, sorting portions of the cultured transfected cells at selected time intervals based on the presence of the replicon RNA or a portion thereof, or the expression of a gene product encoded by the replicon RNA, separately culturing the sorted portions of the transfected cells for a second predetermined period of time, and optionally repeating the steps of sorting and culturing the transfected cells for subsequent predetermined length(s) of time.

In some embodiments, the synthetic replicon construct encodes non-structural proteins for replication, but does not encode structural proteins for viral formation. In further embodiments, the synthetic replicon construct is a self-replicating RNA engineered from alphaviruses. In further embodiments, the synthetic replicon construct is engineered from the Venezuelan equine encephalitis virus. In some embodiments, the synthetic replicon construct includes the untranslated regions, non-structural proteins, and subgenomic promoter of the alphavirus.

In some embodiments, the structural proteins of the synthetic replicon construct are replaced by one or more gene(s) of experimental or therapeutic interest, wherein the one or more gene(s) of experimental or therapeutic interest encode experimental or therapeutic agents. In some embodiments, the experimental or therapeutic agents are cytokines, chemokines, or growth factors. In some embodiments, the experimental or therapeutic agent is Interleukin-2 (IL-2). In alternate embodiments, the experimental or therapeutic agent is luciferase.

In alternative embodiments, the synthetic replicon construct is engineered to express a detectable molecule in the subgenomic region of the synthetic replicon construct. In some embodiments, the detectable molecule is a nucleic acid or polypeptide. In some embodiments, the polypeptide is a fluorescent protein. In further embodiments, the fluorescent protein is selected from a group including, but not limited to, mCherry, mKate, blue fluorescent protein, yellow fluorescent protein, red fluorescent protein, mVenus, green fluorescent protein, mRaspberry, and mStrawberry.

In some embodiments, the replicon RNA is transcribed by in vitro transcription (IVT) from a linearized viral vector by a polymerase. In some embodiments, the polymerase is a T7 RNA polymerase.

In some embodiments, the cells with interferon responses into which the synthesized replicon RNA is transfected are selected from a group including, but not limited to, Jurkat, RAW264.7, or DC2.4 cells.

In some embodiments, the first predetermined length of time is between 40 and 80 days, inclusive, optionally 60 days. In some embodiments, the second predetermined length of time is between 40 and 80 days, inclusive, optionally 60 days.

In some embodiments, the gene product encoded by the replicon RNA is a fluorescent protein, wherein portions of the cultured transfected cells expressing fluorescence are sorted by fluorescence-activated cell sorting at predetermined time intervals.

In some embodiments, the sorted cultured transfected cells expressing the top 1-30%, optionally the top 20%, of fluorescence are selected.

In further embodiments, the portions of the cultured transfected cells expressing fluorescence are sorted at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days following the beginning of the first predetermined length of time, the second predetermined length of time, or any subsequent predetermined length of time.

In some embodiments, the steps of sorting and culturing the sorted cells are repeated between 1 and 10 times, optionally 6 times.

In some aspects, the disclosure provides methods of identifying mutations that increase transfected RNA replicon persistence and/or transfected RNA replicon expression strength in host cells. The methods include extracting the total RNA from sorted cultured transfected cells, reverse-transcribing the extracted total RNA to complementary deoxyribonucleic acid (cDNA), amplifying one or more regions of the alphavirus cDNA, cloning the amplified regions into a vector to produce a cDNA library, and sequencing the cDNA library to identify the mutation(s). In some embodiments, the sorted cultured transfected cells express a fluorescent protein. In some embodiments, the sorted cultured transfected cells express the top 1-30%, optionally the top 20% of fluorescence. In some embodiments, the one or more regions of alphavirus cDNA are regions E1-E7. In some embodiments, the sequencing of the cDNA library to identify mutations is done with at least 6-fold coverage.

In some aspects, the disclosure provides methods of testing a synthetic ribonucleic acid (RNA) replicon. The methods include transfecting an RNA replicon that includes mutation(s) of interest, and tracking the expression of a gene product encoded by the mutated replicon RNA. In some embodiments, the steps of transfecting and tracking are repeated for each identified sequenced mutation in the replicon RNA, or any combination thereof. In some embodiments tracking is for a period of time, optionally 7 days. In some embodiments the tracking is done with flow cytometry.

In some embodiments, the sequenced mutations in the replicon RNA are transfected into Jurkat cells. In some embodiments, the sequenced mutations in the replicon RNA are transfected into RAW-Lucia™ ISG cells.

In some embodiments, the mutation in the replicon RNA encodes for a detectable molecule. In some embodiments, the detectable molecule is a fluorescent protein selected from a group including, but not limited to, mCherry mKate, blue fluorescent protein, yellow fluorescent protein, red fluorescent protein, mVenus, green fluorescent protein, mRaspberry, or mCherry.

In some embodiments, the strength and duration of the fluorescent protein expression in the transfected cells containing the sequenced mutations is compared to the fluorescent protein expression in the cells expressing the wild-type replicon.

In some aspects, the disclosure provides methods of expressing mutated synthetic ribonucleic acid (RNA) replicons in vivo. The methods include preparing equimolar mixtures of mutated synthetic RNA replicons as described herein, encapsulating the prepared equimolar mixtures in lipid nanoparticles, and injecting the lipid nanoparticles into an animal model. In some embodiments, the lipid nanoparticles containing the mutated RNA replicons are in the form of a pharmaceutical composition. In some embodiments, the lipid nanoparticles containing the mutated RNA replicons are injected intratumorally. In some embodiments, the lipid nanoparticles containing the mutated RNA replicons are injected intramuscularly.

In some embodiments, the animal model is a model of human disease, optionally a mouse model. In some embodiments, the animal model is a model of cancer. In one embodiments, the model of cancer is a mouse model of B16F10 melanoma.

In some embodiments, the mutated RNA replicons of interest express an oxidative enzyme in the subgenomic region that produces bioluminescence. In one embodiment, the oxidative enzyme in the subgenomic region that produces bioluminescence is luciferase.

In alternate embodiments, the mutated replicons of interest express any one or more of cytokines, chemokines, growth factors, or reporter fluorescence proteins in the subgenomic region. In some embodiments, the cytokine or growth factor is Interleukin-2 (IL-2). In some embodiments, the reporter fluorescence protein is selected from a group including, but not limited to, mCherry, mKate, blue fluorescent protein, yellow fluorescent protein, red fluorescent protein, mVenus, green fluorescent protein, mRaspberry, and mStrawberry.

In some aspects, the disclosure provides methods of comparing the persistence of mutations occurring in mutated synthetic RNA replicons to wild-type replicons. The methods include isolating replicon RNA from the injected animal model after a predetermined length of time, reverse-transcribing the extracted RNA to complementary deoxyribonucleic acid (cDNA), amplifying one or more regions, sequencing the cDNA library to determine the persistence of the mutated synthetic RNA replicons, and comparing the persistence of the mutated synthetic RNA replicons to the persistence of wild-type replicons assayed using the same animal model. In some embodiments, the one or more regions are regions E1-E7. In some embodiments, sequencing the cDNA library is done with at least 6-fold coverage.

According to one aspect, the disclosure provides methods of comparing the strength of mutations occurring in the mutated RNA replicons to wild-type replicons by comparing the relative strength of luciferase bioluminescence of the mutated RNA replicon injected sites to the wild-type RNA replicon injected sites at predetermined time intervals. In some embodiments, the predetermined time interval is once a day for seven days. In further embodiments, the mutated RNA replicons are engineered from alphaviruses. In further embodiments, the mutated RNA replicons are engineered from the Venezuelan equine encephalitis virus.

According to another aspect, nucleic acid molecules are provided that include a nucleotide sequence as shown in any one of SEQ ID NOs: 1-18. In some embodiments, combinations of the described nucleic acid molecules are used. Combinations of nucleic acid molecules may result in different therapeutic utility than mutations examined alone. In some embodiments, a nucleic acid molecule including a portion of a nucleotide sequence as shown in any one of SEQ ID NOs: 1-18 is used, and the portion of the nucleotide sequence includes a mutation relative to the corresponding wild-type VEE virus RNA. In some embodiments, combinations of the described portions of a nucleotide sequences are used. In some embodiments, the portion of the nucleotide sequence is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, or 1000 nucleotides in length.

The subject matter of this application may involve, in some cases, interrelated products, alternative solutions to a particular problem, and/or a plurality of different uses of a single system or article. These and other aspects of this disclosure, as well as various embodiments thereof, will become more apparent in reference to the drawings and detailed description. Additionally, the subject matter disclosed herein is not limited in its application to the details of construction and the arrangement of components set forth in the following description or illustrated in the drawings. It is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

FIGS. 1A-1C. Identification of mutant replicons promoting subgenome expression by in vitro evolution. (FIG. 1A) Method for in vitro replicon evolution: Jurkat cells were transfected with replicon RNA encoding mCherry under the SGP and placed in cell culture. The top 20% of the mCherry positive population were sorted approximately every 10 days during serial passaging as indicated by the flow cytometry histograms, leading to an enrichment in cells expressing high levels of the reporter gene. Cells from the $5^{th}$ sort were isolated for replicon sequencing. (FIG. 1B) Identification of mutations: Total RNA from mCherry positive cells was extracted and reverse transcribed to cDNA. Then, nsP1-4 and the subgenomic promoter were amplified by seven pairs of specific primers and amplicons from Loci 1-7 were engineered into plasmid DNA and transformed into *E. coli* for amplification. Six clones from each locus were randomly picked for Sanger Sequencing. Schematic at bottom left shows the approximate locations in nsP2 and nsP3 where point mutations were identified in 5 mutant alleles with $c_2$ harboring two linked mutations. (FIG. 1C) Table describing the 5 mutant alleles identified in the screen. Mutation rate are the percentages of mutations in the locus to be sequenced.

(FIG. 2F) Scatter plot of maximal mCherry MFI vs. the rate of decay of $mCherry^+$ cells for all replicons tested. mCherry decay rate was calculated by subtracting the percentage of mCherry+ cells at day 7 from that at day 1, and dividing by 7. The promising mutants and WT replicons were highlighted as orange and red for later studying, respectively.

(FIGS. 3A-3B) Subgenomic RNA levels of mCherry RNA generally correlated with the nsP RNA levels. (FIG. 3C) The ratios of mCherry to nsP transcripts in cells transfected with replicon RNA as indicated. (FIG. 3D) Scatter plot of MFI of mCherry vs. the relative mCherry transcripts in Jurkat cells at 5 day for all replicons tested. Coefficient of determination (R-squared) was indicated. (FIG. 3E) RAW-Lucia™ ISG reporter cells were transfected with replicons and the interferon response and mCherry fluorescence levels were observed after 24 hours via bioluminescence and flow cytometry, respectively. Certain mutants and WT replicons were highlighted as orange and red for additional study, respectively.

(FIG. 4A) C57B1/6 mice (n=4/group) bearing B16F10 tumors ~50 $mm^2$ in size were injected intratumorally with 10 μg lipid nanoparticle-formulated WT or mutant replicons encoding luciferase, and bioluminescence was tracked over time. (FIG. 4B) C57B1/6 mice (n=4/group) were injected intramuscularly with 2.5 μg lipid nanoparticle-formulated WT or mutant replicons encoding luciferase, and bioluminescence was tracked over time. Statistics were analyzed by two-way ANOVA. * and ** denote p-value <0.05 and <0.01, respectively.

(FIG. 5A) B16F10 melanoma cells were transfected with WT or mutant replicons encoding IL-2, and secreted IL-2 present in the supernatants was measured over 3 days by ELISA. Statistics were analyzed by two-way ANOVA. * and ** denote p-value <0.05 and <0.01, respectively. (FIGS. 5B-5C) Groups of C57B1/6 mice (n=4/group) bearing B16F10 tumors ~50 $mm^2$ in size were injected intratumorally with 10 μg lipid nanoparticle-formulated IL-2-encoding replicons (ABC-IL2, or $Ab_1c_1$-IL2) or WT (ABC) control replicon with no subgenome cargo. Transcripts of IL-2 within the tumors were measured by PCR 3 days post injection (FIG. 5B), and total numbers of CD8 T cells were enumerated in tumors at 3 days post lipid nanoparticle-replicon injection (FIG. 5C). Statistics were analyzed by one-way ANOVA. * and ** denotes p-value <0.05 and <0.01, respectively. (FIGS. 5D-5E) C57B1/6 mice (n=5/group) were injected subcutaneously in the flank with $10^6$ B16F10 cells, and then received intratumoral injections of 10 μg lipid nanoparticle-formulated WT control or IL-2-encoding replicons on day 7 (FIG. 5D) or on days 7, 9, and 11 (FIG. 5E). Shown are average tumor growth (FIG. 5D) and overall survival (FIG. 5E). Statistics for survival cure (FIG. 5E) were analyzed by Curve Comparison. * denotes a p-value <0.05.

(FIG. 6A) Percentages and (FIG. 6B) MFI of mCherry+ cells prior to each sort.

DETAILED DESCRIPTION

Figure 2A:
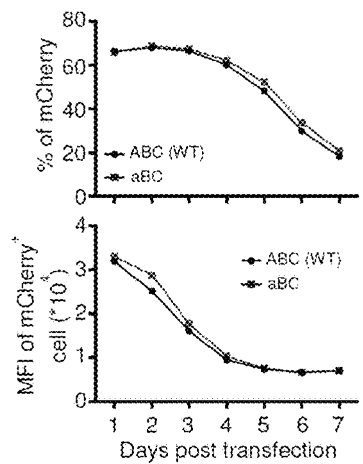
FIGS. 2A-2F. Mutations in alleles $b_1$, $b_2$, $c_1$ and $c_2$ impact the intensity and longevity of transgene expression. Jurkat cells were transfected with WT or mutant replicons encoding mCherry as a reporter and then cultured for 7 days. The mean fluorescence intensities (MFI) and the percentage of $mCherry^+$ positive cells were tracked over time by flow cytometry. Shown are comparisons of WT with replicons containing mutant alleles a (FIG. 2A), $b_1$ and $b_2$ (FIG. 2B), $c_1$ and $c_2$ (FIG. 2C), or combinations of alleles $c_1$ and $c_2$ with $b_1$ (FIG. 2D) or $b_2$ (FIG. 2E). MFI of $mCherry^+$ cells are shown with a y-axis range of either 0-4.0×$10^4$ or 0-1.5'$10^5$ to highlight difference relative to WT replicon.

In the present disclosure, alphavirus replicons encoding therapeutic genes or antigens under the subgenomic promoter, in place of the structural proteins required for virus replication, are of substantial interest as platforms for gene therapy and vaccination. To increase the effectiveness of replicon RNA, an in vitro evolution (IVE) strategy was employed to identify mutations in alphavirus replicons that enhanced the strength and persistence of gene expression from the replicon's subgenomic promoter in the cells of a subject.

A virus is a small pathogen that is only capable of replication inside a living host cell (e.g., prokaryotic and eukaryotic cells). Outside of living cells, viruses exist as independent particles (e.g., viral particles or virions), which comprise genetic material in the form of DNA or RNA, the latter of which can be single-stranded or double-stranded. Viruses with DNA are referred to as DNA viruses, and viruses with RNA are referred to as RNA viruses. In some cases, the virus comprises nucleic acid-associated proteins and the combination of the virus and nucleic acid-associated proteins is referred to as nucleoprotein. In addition to the genetic material, viruses have a single or double protein coat, also known as a capsid, which facilitates attachment of the virus to a living host cell's receptors during infection and protects the genetic material of the virus from enzymatic degradation. The combination of nucleoprotein and the capsid is referred to as a nucleocapsid. In some cases, viruses have a lipid bilayer envelope, studded with virus-coded, glycosylated (trans-) membrane-associated proteins. Once a virus has infected a living host cell, the virus is dependent on the living host cell to supply the machinery for its replication, and propagation thereafter. The viral genome codes for some structural proteins and non-structural regulatory proteins.[24]

The term "structural protein," as used in the context of viruses herein, refers to proteins that constitute the structural components of mature assembled virus particles or virions. Non-limiting examples of such structural proteins include nucleocapsid core proteins (e.g., gag proteins), enzymes packaged within the virus particle (e.g., pol proteins), and membrane components (e.g., env proteins). In contrast, the term "non-structural protein," as used in the context of viruses herein, refer to proteins that are expressed within the host cell but do not constitute structural components of the virus particle or virion. Some of the roles of non-structural proteins include, but are not limited to, replicon formation, immunomodulation, and transactivation of structural protein genes.[25]

As used herein, the term "replicon" refers to a self-replicating genetic element comprised of DNA or RNA that replicates from one origin of replication. In some embodiments, the replicon is a viral replicon. In some embodiments, the replicon is an alphavirus replicon. Distinct from host mRNA, alphavirus replicon RNAs encode a set of four nonstructural proteins (nsPs 1-4) that are responsible both for genome replication and, when engineered to include genes encoding non-virus products, such as "cargo" proteins, provide for transcription of such "cargo" products under the subgenomic promoter.

Alphaviruses are part of the IV Togaviridae family of viruses, possess a positive sense, single-stranded RNA genome, and are characterized by an icosahedral nucleocapsid. The alphavirus genus includes 26 enveloped viruses that infect eukaryotes. Alphaviruses have a broad host range and are transmitted by mosquitos and hematophagous arthropods. Non-limiting examples of alphaviruses include Venezuelan equine encephalitis (VEE), Eastern Equine Encephalitis (EEE), Western equine encephalitis (WEE), Everglades (EVE), Mucambo (MUC), Pixuna (PIX), Semliki Forest (SF), Middelburg (MID), Chikungunya (CHIK), O'Nyong-Nyong (ONN), Ross River (RR), Barmah Forest (BF), Getah (GET), Sagiyama (SAG), Bebaru (BEB), Mayaro (MAY), Una (UNA), Sindbis (SIN), Aura (AURA), Babanki (BAB), Highlands J (HJ), and Fort Morgan (FM).

In the present disclosure, the alphavirus replicon is a VEE alphavirus replicon. The VEE virus is a viral pathogen typically carried by mosquitos that causes VEE or encephalomyelitis predominately in equine species. Humans, however, may also contract VEE, and people with weakened immune systems are especially at risk of having severe complications if infected with VEE. The virion of VEE is spherical and possesses a lipid membrane with glycoprotein surface proteins spread around the outer surface. Typically, VEE has a genome of approximately 11.45 kb, excluding the 5'-terminal cap and 3'-terminal poly(A) tract, and comprises 4 nonstructural proteins (nsPs) and 5 structural proteins. The non-structural proteins include nsP1, nsP2, nsP3, and nsP4, while the structural region encodes proteins C, E3, E2, 6K, and E1.[26,27]

Of the non-structural proteins, nsP1 is required for initiation of synthesis of minus-strand RNA, nsP2 has been shown to be regulate the synthesis of the 26S subgenomic RNA and regulate the cytopathic effect of alphavirus infection.[28,29] The role of nsP3 role is not well understood but prior art focused on SIN alphavirus suggests that it is involved in subgenomic transcription.[30] nsP4 has been shown to encode the RNA polymerase of the alphavirus. In one embodiment, the VEE alphavirus replicon has non-structural proteins present, but has genes encoding its structural proteins deleted.

As used herein, the term "deleted" or "deletion" refers to total deletion of the specified segment or the deletion of a sufficient portion of the specified segment to render the segment inoperative or nonfunctional. Methods for deletion are well established in the art can be found in U.S. Pat. No. 4,650,764.[31]

As used herein, the term "subgenome" or "subgenomic" refers to a smaller section of the whole replicon genome. Accordingly, subgenomic transcription, as used herein, refers to the transcription of one or more genes in the replicon genome but not all the genes constituting the replicon genome. In one embodiment, subgenomic transcription refers to transcription of the genes of experimental or therapeutic interest, which are described elsewhere herein.

The present disclosure includes methods for in vitro evolution (IVE) of replicons derived from viruses using engineered synthetic replicons. The terms "synthesized" and "engineered" are used interchangeably herein. As used herein, the term "synthetic" refers to a replicon that, following transfection, will not result in the production of viral particles or packaging. In some embodiments, the synthetic RNA replicons are engineered from alphaviruses. In one embodiment, the alphavirus is VEE.

"Evolution" as used herein refers to the selection of cells based on a desired trait, wherein the desired trait can be the expression of a detection molecule (e.g., a fluorophore) or expression of an experimental or therapeutic agent. As described herein, the experimental or therapeutic agent is encoded by a gene, optionally naturally occurring, optionally cloned into a vector, or optionally cloned into a replicon. Non-limiting examples of therapeutic agents include cytokines, chemokines, and growth factors, which are described elsewhere herein.

Disclosed herein are methods of in vitro evolution to identify synthetic mutations in self-replicating ribonucleic acid (RNA). Self-replicating RNA (replicon) is a promising new platform for gene therapy, but applications are still limited by short persistence of expression in some cell types and low levels of transgene expression in vivo. The methods of in vitro evolution disclosed herein allow for the identification and repeated culturing of specific mutations in synthetic replicon RNA that increase the persistence and level of expression of engineered replicons in vivo. When coupled with emerging methods for effective delivery of purified replicon RNAs using synthetic formulations,[12] this in vitro evolution of nsPs within synthetic replicon RNA provides a potentially powerful strategy for modifying and enhancing replicon expression both in vitro and in vivo. To this end, the methods disclosed herein utilize replicon constructs with the structural proteins deleted, which allows for the discovery of mutations in the nsPs that impact the persistence of replicon RNA and the strength of gene expression from the subgenome rather than viral particle production/packaging. Using the method of in vitro evolution disclosed herein, six mutations were identified in nsP2 and nsP3 of Venezuelan equine encephalitis (VEE) replicon that promoted subgenomic expression in human cells.

According to one aspect, a method for in vitro evolution of synthetic replicon RNA is provided. The method includes engineering and synthesizing a synthetic replicon that encodes replicon RNA. Next, the synthesized replicon RNA is transfected into cells that exhibit an interferon response. These cells with an interferon response are cultured for a length of time, which is predetermined. After that first predetermined length of time has expired, the cultured cells containing the transfected replicon RNA are sorted based on the presence of either the replicon RNA, or a portion thereof, or on the expression of a gene product that was encoded by the replicon RNA. This step of sorting is performed at time intervals that are preselected. After the transfected cells are sorted, the portion of the cell culture containing the targeted gene product or replicon RNA is cultured separately from the original culture. This second culture of the sorted transfected cells is performed for a second predetermined length of time, which may be the same or different from the length of time of the original culture. The aforementioned processes of sorting and culturing may be repeated any number of times, wherein each length of culture time and the length of time between sorts is predetermined, and may be the same or different from previous evolutions.

As used herein, the term "transfection" refers to the artificial delivery and introduction of nucleic acids (optionally RNA; optionally DNA), into a cell (e.g., eukaryotic cell). In one embodiment, the cell (e.g., host cell) that undergoes transfection is a eukaryotic cell from a subject, examples of which are provided herein. As used herein, the term "host cell" refers to any cell which can be transfected with an exogenous nucleic acid. The process of transfection can impart new properties to the host cell. The delivery and introduction of nucleic acid into the cell allows it to express the nucleic acid, transiently or stably. "Transient gene expression" refers to expression by a cell of a nucleic acid that is not integrated into the nuclear genome of the cell. By comparison, "stable gene expression" refers to expression by a cell of a nucleic acid that remains in the nuclear genome of the cell and its daughter cells. Typically, to achieve stable gene expression, a cell is co-transfected with a marker gene and an exogenous nucleic acid that is intended for stable expression in the cell.

Methods of transfection are well established in the arts and range from chemical, to biological, and to physical methods. Chemical methods include, but are not limited to, calcium phosphate transfection, cationic polymer transfection, lipofection, FUGENE®, and DEAE-Dextran-mediated transfection. Other methods of transfection include, but are not limited to, electroporation (e.g., by using a Neon® transfection system), sonoporation, cell squeezing, impalefection, optical transfection, protoplast fusion, Magnetofection™, and particle bombardment.

As described herein, cells are transfected with the alphavirus replicon. Non-limiting examples of cells that can undergo the transfection described herein include Jurkat cells, RAW-Lucia™ ISG cells, DC2.4 cells, CD8 T cells, B16F10 tumor cells, and BHK-21 cells. Additional non-limiting examples of cells that can undergo alphavirus replicon transfection include neuronal cells, retinal cells, epithelial cells, muscle cells, pancreatic cells, hepatic cells, fibroblasts, endothelial cells, germ cells, lung cells, prostate cells, stem cells, progenitor cells, dendritic cells, and immunomodulatory cells. These cells can be from any subject, as described elsewhere herein.

"Cell sorting", as used herein, refers to the process of separating cells, optionally from a heterogeneous population, based on the cells' characteristics (e.g., separation criteria). Separation criteria include, but are not limited to, cell size, cell shape, cell protein expression (including expression of fluorescent proteins), and cell buoyancy. Non-limiting examples of cell sorting techniques include, but are not limited to, magnetic cell sorting, flow cytometry, and microchip sorting. In some embodiments, flow cytometry encompasses the use of fluorescence-activated cell sorting (FACS), which is a method of sorting cells based on the cells' expression of a fluorophore. In FACS, cells are sorted one cell at a time, into multiple containers based on light scattering and the fluorescent properties of each cell.

Cells expressing the genetic constructs described herein may be cultured (e.g., maintained in cell culture) using conventional cell culture methods. For example, cells may be grown and maintained at an appropriate temperature and gas mixture (e.g., 37° C., 5% CO2 for mammalian cells) in a cell incubator. In some embodiments, the cells may be incubated under specific conditions to induce a desired state of the cell, such as a development state, activation or disease state. Culture conditions may vary for each cell type. For example, cell growth media may vary in pH, glucose concentration, growth factors, and the presence of other nutrients. Growth factors used to supplement media are often derived from the serum of animal blood, such as fetal bovine serum (FBS), bovine calf serum, equine serum and/or porcine serum. In some embodiments, culture media used as provided herein may be commercially available and/or well-described (see, e.g., Birch J. R., R. G. Spier (Ed.) Encyclopedia of Cell Technology, Wiley. 411-424, 2000; Keen M. J. Cytotechnology (1995) 17:125-132; Zang, et al. Bio/Technology (1995) 13:389-392). In some embodiments, chemically defined media is used.

In some embodiments, the synthetic replicon construct encodes non-structural proteins for replication, but does not encode structural proteins for viral formation. In some embodiments, the synthetic replicon construct is a self-replicating RNA engineered from alphaviruses. In some embodiments, the synthetic replicon construct includes the untranslated regions, non-structural proteins, and subgenomic promoter of the alphavirus.

In some embodiments, the structural proteins of the synthetic replicon construct are replaced by one or more gene(s) of experimental or therapeutic interest. In some embodiments, the gene(s) of experimental or therapeutic interest encode cytokines, chemokines, or growth factors. Cytokines are known in the art, and the term itself refers to a generalized grouping of small proteins that are secreted by certain cells within the immune system and have an effect on other cells. Cytokines are known to enhance the cellular immune response and, as used herein, can include, but are not limited to, TNFα, IFN-γ, IFN-α, TGF-β, IL-1, IL-2, IL-4, IL-10, IL-13, IL-17, IL-18, and chemokines. Chemokines are useful for studies investigating response to infection, immune responses, inflammation, trauma, sepsis, cancer, and reproduction, among other applications. Chemokines are known in the art, and are a type of cytokines that induce chemotaxis in nearby responsive cells, typically of white blood cells, to sites of infection. Non-limiting examples of chemokines include, CCL14, CCL19, CCL20, CCL21, CCL25, CCL27, CXCL12, CXCL13, CXCL-8, CCL2, CCL3, CCL4, CCL5, CCL11, and CXCL10. Growth factors are known in the art, and the term itself is sometimes interchangeable with the term cytokines. As used herein, the term "growth factors" refers to a naturally occurring substance capable of signaling between cells and stimulating cellular growth. While cytokines may be growth factors, certain types of cytokines may also have an inhibitory effect on cell growth, thus differentiating the two terms. Non-limiting examples of growth factors include Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 1(FGF1), Fibroblast growth factor 2(FGF2), Fibroblast growth factor 3(FGF3), Fibroblast growth factor 4(FGF4), Fibroblast growth factor 5(FGF5), Fibroblast growth factor 6(FGF6), Fibroblast growth factor 7(FGF7), Fibroblast growth factor 8(FGF8), Fibroblast growth factor 9(FGF9), Fibroblast growth factor 10(FGF10), Fibroblast growth factor 11(FGF11), Fibroblast growth factor 12(FGF12), Fibroblast growth factor 13(FGF13), Fibroblast growth factor 14(FGF14), Fibroblast growth factor 15(FGF15), Fibroblast growth factor 16(FGF16), Fibroblast growth factor 17(FGF17), Fibroblast growth factor 18(FGF18), Fibroblast growth factor 19(FGF19), Fibroblast growth factor 20(FGF20), Fibroblast growth factor 21(FGF21), Fibroblast growth factor 22(FGF22), Fibroblast growth factor 23(FGF23), Fetal Bovine Somatotrophin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Interleukin-1 (IL-1), IL-2, IL-3, IL-4, IL-5, IL-6, IL-7, Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), and Vascular endothelial growth factor (VEGF).

In some embodiments, the gene of experimental or therapeutic interest encodes Interleukin-2 (IL-2), a type of cytokine signaling molecule in the immune system that is known to regulate the activities of white blood cells that are responsible for immunity. In some embodiments, the gene of experimental or therapeutic interest encodes luciferase. Luciferase is a generalized term known in the art that refers to the class of oxidative enzymes that produce bioluminescence, and is typically distinct from photoproteins and/or fluorophores/fluorescent proteins. The interaction of luciferase and its consumable substrate, luciferin, is required for bioluminescence.

In some embodiments, the synthetic replicon construct is engineered to express a detectable molecule in the subgenomic region of the synthetic replicon construct. In some embodiments, the detectable molecule is a nucleic acid or a polypeptide. In some embodiments, the polypeptide is a fluorescent protein. Fluorescent proteins are known in the art, and are a subclass of fluorophores, which are fluorescent chemical compounds with the ability to re-emit light upon excitation. The fluorophore will absorb excitation light energy of a first specific wavelength, and then will re-emit light energy at a second, longer specific wavelength. Each type of fluorophore responds to and emits differing wavelengths of light, depending on the nature of its chemical structure and environment. In some embodiments, the fluorescent protein includes, but is not limited to, wt-GFP, green fluorescent protein (e.g, EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.).

In some embodiments, the replicon RNA is transcribed by in vitro transcription (IVT) from a linearized viral vector by a polymerase. Transcription is known in the art, and is the first step of gene expression, wherein a segment of deoxyribonucleic acid (DNA) is copied into RNA by an RNA polymerase. In some embodiments, the polymerase is a T7 RNA polymerase, which catalyzes the formation of RNA from DNA in the 5' to 3' direction. The T7 RNA polymerase is from the T7 bacteriophage.

Interferon-deficient BHK-21 cells have often been used in alphavirus studies, as type I interferons strongly restrict replicon expression.[32] Herein, IVE was performed in Jurkat cells that maintain an intact interferon response in order to allow for the possibility of selecting mutants with altered interferon induction. In alternative embodiments, IVE is performed in a different type of cell, examples of which are provided elsewhere herein.

In some embodiments, the cells with interferon responses into which the synthesized replicon RNA is transfected are Jurkat, RAW264.7, or DC2.4 cells. Interferon response results from the release of interferons, a type of signaling protein, from host cells in response to pathogens, such as viruses, bacteria, parasites, and tumor cells. Jurkat cells, which possess an interferon response, are a known line of human T lymphocyte cells that are often used to study T-cell receptor signaling, and have been useful in studying acute T cell leukemia, T cell signaling, and chemokines—specifically chemokines that are susceptible to viral entry. Jurkat cells possess a robust ability to produce IL-2. Jurkat cells also have utility in research pertaining to protein expression, viral interactions, and cancer biochemistry, among several other potential utilities. RAW264.7 cells also possess an interferon response, and are a known murine macrophage line. RAW264.7 cells are often used to screen for the bioactivity of natural products and predict the potential effect of the products in vivo. RAW264.7 cells are typically thought to mirror the potential response of human cells to novel therapeutic interventions. In this capacity, RAW264.7 cells may be used to assess the bioactivity of the natural product.[33] DC2.4 cells also possess an interferon response, and are a known line of mouse murine dendritic cells. Dendritic cells (DC) are found in most tissues, and are the antigen presenting cells of the immune system. Because of the endogenous immune function of dendritic cells, the cell line is useful for studies on various aspects of immune response mechanisms.

In some embodiments, the first predetermined length of time, during which the first batch of transfected cells are cultured, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days. In one embodiment, the first predetermined length of time is 60 days.

In some embodiments, where the gene product encoded by the replicon RNA is a fluorescent protein, portions of the cultured transfected cells expressing fluorescence are sorted by fluorescence-activated cell sorting (FACS) at predetermined time intervals. In some embodiments, the sorted cultured transfected cells expressing the top 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of fluorescence are selected by FACS. In one embodiment, cells expressing the top 20%, of fluorescence are selected. In some embodiments, the cultured transfected cells expressing fluorescence are sorted by FACS at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days. 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or 50 days following the beginning of the first predetermined length of time. In one embodiment, the cultured transfected cells expressing fluorescence are sorted by FACS at 10 days following the beginning of the first predetermined length of time.

In some embodiments, after the transfected cells are sorted by FACS, the portion of the cell culture containing the targeted gene product or replicon RNA is re-cultured separately from the original culture for a second predetermined length of time. In some embodiments, the second predetermined length of time, during which the selected cells are re-cultured, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days. In one embodiment, the second predetermined length of time is 60 days.

In some embodiments, where the gene product encoded by the replicon RNA is a fluorescent protein, portions of the re-cultured transfected cells expressing fluorescence are re-sorted by FACS at predetermined time intervals. In some embodiments, the re-cultured transfected cells expressing fluorescence are re-sorted by FACS at 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days. 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, or 50 days following the beginning of the second predetermined length of time. In one embodiment, the re-cultured transfected cells expressing fluorescence are re-sorted by FACS at 10 days following the beginning of the second predetermined length of time.

In some embodiments, the steps of sorting, re-culturing, and re-sorting, may be repeated ad infinitum. In some embodiments, the steps are repeated 1, 2, 3, 4, 5, 6, 7, 8, 9, 10, 11, 12, 13, 14, 15, 16, 17, 18, 19, or 20 time(s). In one embodiment, the steps are repeated 6 times.

In some embodiments, mutations that increase transfected RNA replicon persistence and/or transfected RNA replicon expression strength in host cells are identified. First, the total RNA is extracted from the sorted cultured transfected cells expressing the top 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% of fluorescence. In one embodiment, the total RNA is extracted from the sorted cultured transfected cells expressing the top 20% of fluorescence. Second, the extracted total RNA is reverse transcribed to complementary deoxyribonucleic acid (cDNA). Third, one or more regions (e.g., loci) of the VEE cDNA are amplified. In one embodiment, seven regions (E1-E7) of the VEE cDNA are amplified. Fourth, the amplified regions are cloned into a vector to produce a cDNA library. Finally, the cDNA library is sequenced in order to identify the mutation(s). In one embodiment, the cDNA library is sequenced with 6-fold coverage.

The term "clone," as used herein, refers to the incorporation of a gene locus, gene, gene sequence or other nucleic acid molecule into a vector (i.e., cloning vector). As used herein, a "vector" may be any of a number of nucleic acids into which a desired sequence or sequences may be inserted, for example, by restriction digestion and ligation or by recombination for transport between different genetic environments or for expression in a host cell. Vectors are typically composed of DNA, although RNA vectors are also available. Examples of vectors include, but are not limited to plasmids, fosmids, phage lambda, cosmids, single stranded phages, expression vectors, and artificial chromosomes.[34] Cloning, or molecular cloning is known in the art (see, e.g., Current Protocols in Molecular Biology, Ausubel, F. M., et al., New York: John Wiley & Sons, 2006; Molecular Cloning: A Laboratory Manual, Green, M. R. and Sambrook J., New York: Cold Spring Harbor Laboratory Press, 2012; Gibson, D. G., et al., Nature Methods 6(5):343-345 (2009), the teachings of which relating to molecular cloning are herein incorporated by reference).

According to another aspect, a method of testing a synthetic ribonucleic acid (RNA) replicon is provided. The method includes transfecting an RNA replicon into cells, wherein the RNA replicon contains the specific mutations, or combinations thereof, identified using the methodology described above. The expression of a gene product, or products, encoded by the mutated replicon RNA is then tracked. In some embodiments, the steps of transfecting and tracking are repeated for each identified sequenced mutation in the replicon RNA, or any combination thereof.

In some embodiments, the sequenced mutations in the replicon RNA are transfected into Jurkat cells. In some embodiments, the sequenced mutations in the replicon RNA are transfected into RAW-Lucia™ ISG cells. RAW-Lucia™ ISG cells are generated from the murine RAW 264.7 macrophage cell line, described above, by stable integration of an interferon regulatory factor-inducible Lucia luciferase reporter construct. Thus, RAW-Lucia™ ISG cells allow for the monitoring of interferon regulatory factor activation by reporting the activity of Lucia luciferase.

In some embodiments, the expression of the fluorescent protein associated with the mutation in the replicon RNA is tracked for a period of time using flow cytometry. In those embodiments, the fluorescent protein is as described elsewhere herein. In some embodiments, the expression of the fluorescent protein is tracked for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days. In one embodiment, expression of the fluorescent protein is tracked for 7 days.

In some embodiments, the strength and duration of the fluorescent protein expression in the transfected cells containing the sequenced mutations is compared to the fluorescent protein expression in the cells expressing the wild-type replicon. This comparison allows for the assessment of the therapeutic utility of the identified mutations, and combinations thereof.

According to another aspect, a method of expressing mutated synthetic ribonucleic acid (RNA) replicons in vivo is provided. The method includes preparing equimolar mixtures of mutated synthetic RNA replicons that were identified and produced by the methods described herein, encapsulating the prepared equimolar mixtures in lipid nanoparticles (LNPs), and administering the lipid nanoparticles into a subject. The disclosed method can apply in an experimental, veterinary, and medical context. In some embodiments the subject is a human. In some embodiments, the subject is an animal (e.g., animal model). In other embodiments the subject is a mouse. Subjects also include animals such as household pets (e.g., dogs, cats, rabbits, ferrets, etc.), livestock or farm animals (e.g., cows, pigs, sheep, chickens and other poultry), horses such as thoroughbred horses, laboratory animals (e.g., rats, rabbits, etc.), and the like.

In some embodiments, the mutated synthetic RNA replicons of interest express an oxidative enzyme in the subgenomic region that produces bioluminescence. In one embodiment, the oxidative enzyme that produces bioluminescence is luciferase. In some embodiments, the mutated synthetic RNA replicons of interest express any one of cytokines, chemokines, or growth factors, as well as a reporter fluorescence protein in the subgenomic region. In one embodiment, the mutated synthetic RNA replicons of interest express IL-2. In some embodiments, the fluorescent protein is as described elsewhere herein.

In some embodiments, a method of comparing the persistence of mutations occurring in mutated synthetic RNA replicons to wild-type replicons is described. According to this embodiment, replicon RNA is isolated after a predetermined length of time from the animal model that was injected with lipid nanoparticles containing the mutated RNA replicons as described herein. The extracted RNA is then reverse transcribed to cDNA. Next, one or more regions of the cDNA are amplified. In one embodiment, regions E1-E7 of the cDNA are amplified. The amplified regions are then cloned into a vector to produce a cDNA library. Finally, the cDNA library is sequenced in order to determine the persistence of the mutated synthetic RNA replicons. In one embodiment, the cDNA library is sequenced with 6-fold coverage. Finally, the persistence of the mutated synthetic RNA replicons is compared to the persistence of wild-type replicons assayed using the same animal model.

In some embodiments, a method of comparing the strength of mutations occurring in mutated synthetic RNA replicons to wild-type replicons is described. According to this embodiment, the relative strength of luciferase bioluminescence of the mutated RNA replicon injected sites is compared to the wild-type RNA replicon injected sites at predetermined time intervals. In one embodiment, the predetermined time interval is 7 days.

Lipid-based nanoparticles (LNPs) are a method by which pharmaceutical therapies may be delivered to targeted locations. One example is lipid nanoparticle, which contain a solid lipid core matrix with the ability to solubilize lipophilic molecules. Non-limiting examples of LNPs include liposomes, bolaamphiphiles, solid lipid nanoparticles (SLN), nanostructured lipid carriers (NLC), and monolayer membrane structures (e.g., archaeosomes and micelles).[35]

The lipid nanoparticles described herein can be administered as an injection, using different delivery routes. The lipid nanoparticles of the present disclosure can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated. In a particular embodiment, intratumoral injection is contemplated.

In some embodiments, the animal model is a model of cancer. The cancer can be a carcinoma, a sarcoma or a melanoma. Carcinomas include, but are not limited to, basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system. In one embodiment, the animal model is a mouse model of B16F10 melanoma. B16F10 melanoma is a murine tumor cell line that is used as a model for human skin cancers, and is a useful model for researching therapeutic interventions relating to metastasis and solid tumor formation. In some embodiments, the lipid nanoparticles containing the mutated RNA replicons are injected intratumorally. Intratumorally is a term known in the art, and refers to an injection being placed within a tumor. In some embodiments, the lipid nanoparticles containing the mutated RNA replicons are injected intramuscularly. Intramuscularly is a term known in the art, and refers to an injection being placed within a muscle. In some embodiments, intramuscular injections of nanoparticles containing the mutated RNA replicons are used to examine the utility of the identified mutations for vaccination purposes.

In some embodiments, the lipid nanoparticles are administered by injection in the form of a pharmaceutical composition (e.g., LNP composition). Pharmaceutical compositions are sterile compositions that include cells, nanoparticles and/or agent(s), preferably in a pharmaceutically-acceptable carrier. This term requires that a compound or composition be nontoxic and sufficiently pure so that no further manipulation of the compound or composition is needed prior to administration to the subject. The term "carrier" denotes an organic or inorganic ingredient, natural or synthetic, with which the cells, nanoparticles and agent(s) are combined to facilitate administration. The components of the pharmaceutical compositions are combined in a manner that precludes interaction that would substantially impair their desired pharmaceutical efficiency. Moreover, for animal (e.g., human) administration, it will be understood that preparations should meet sterility, pyrogenicity, general safety and purity standards as required by FDA Office of Biological Standards. The compounds are generally suitable for administration to humans or mammals Compositions for lipid nanoparticles with biological active molecules and suitable carriers are disclosed in U.S. Pat. No. 7,404,969.

The lipid nanoparticles or the LNP composition can be administered once, or alternatively they may be administered in a plurality of administrations. If administered multiple times, the compounds may be administered via different routes. For example, the first (or the first few) administrations may be made directly into the affected tissue while later administrations may be systemic.

As used herein, the term "pharmaceutically-acceptable carrier" refers to one or more compatible solid or liquid filler, diluents or encapsulating substances which are suitable for administration to a human or other subject contemplated by the disclosure. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers (e.g., antioxidants), gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

The following examples are provided to illustrate specific instances of the practice of the present disclosure and are not intended to limit the scope of the invention. As will be apparent to one of ordinary skill in the art, the present invention will find application in a variety of compositions and methods.

EXAMPLES

Materials and Methods

Cell Lines and Animals

Cell lines Jurkat (ATCC® TIB-152™), RAW-Lucia™ ISG (http://www.invivogen.com/raw-lucia-isg), and B16F10 (ATCC® CRL-6475™), were cultured following vendor instructions (37° C., 5% $CO_2$). Female C57BL/6J (JAX Stock No. 000664) mice 6-8 weeks of age were maintained in the animal facility at the Massachusetts Institute of Technology (MIT). All animal studies and procedures were carried out following federal, state, and local guidelines under an IACUC-approved animal protocol.

Constructs, In Vitro Transcription, Capping/Methylating for Replicon RNA, and Neon Transfection Wild type VEE replicon RNA was prepared as described in Wrobleska et al.[17] mCherry was amplified by two round PCR with the primers YL-mCherry-ClaI-F, YL-mCherry-R1, and YL-mCherry-ClaI-F, YL-mCherry-SphI-R2 (Table 2). Fragments from the second round PCR were cloned into the VEE replicon construct[36,37] to obtain plasmids encoding the wild type VEE-mCherry construct.

Replicon RNAs were in vitro transcribed (IVT) from the templates of linearized VEE-constructs above using the MEGAscript™ T7 Transcription Kit (ThermoFisher) following the manufacturer's instructions. Resulting replicon RNAs were capped and methylated using the ScriptCap™ m7G Capping System and ScriptCap™ 2'-O-Methyltransferase Kit (Cellscript) according to the manufacturer's instructions. RNA purity was assessed by gel electrophoresis.

In vitro transfections were carried out using 1 μg RNA for per 200,000 cells using the NEON electroporation kit (ThermoFisher) following the manufacturer's instructions.

In Vitro Evolution Screen

Jurkat cells were transfected with VEE-mCherry replicon RNA using a NEON transfection kit and the cells were cultured in 37° C. with 5% $CO_2$ for 10 days. The 20% cells expressing highest levels of mCherry were then sorted using a BD Aria III sorter, and sorted cells were cultured for 10 days prior to the next sorting. Sorting was repeated through 6 rounds, and the $5^{th}$ round sorted cells were selected for total RNA extraction and cDNA synthesis. Using the cDNA as template, the nsP1-4 and subgenomic promoter regions were divided into 7 overlapping loci, and each loci was amplified by 7 pairs of primers, YL-Locus-5'UTR-F1 and YL-Locus-R1, YL-Locus-F2 and YL-Locus-R2, YL-Locus-F3 and YL-Locus-R3, YL-Locus-F4 and YL-Locus-R4, YL-Locus-F5 and YL-Locus-R5, YL-Locus-F6 and YL-Locus-R6, YL-Locus-F7 and YL Locus-R7, respectively (Table 2). The 7 amplicons were cloned into the BsaI of pTW064MM and transformed into *E. coli* DH5α. Six clones from each locus were picked for Sanger sequencing.

Assembly of Mutant Replicons

Mutations identified in the in vitro evolution screen were cloned into replicons encoding mCherry to obtain mutant replicons for characterization in vitro and in vivo. For cloning mutant allele a into the replicon construct, plasmids L2-4 were digested by SalI and EcoRI for insertion into the wild type replicon construct. The constructs with alleles $b_1$ and $b_2$ were amplified by YL-nsP2-XmaI-F and YL-nsP3-PstI-R from plasmids L4-5 ($b_1$) and L4-3 ($b_2$) to clone into wild type construct (ABC), respectively. For cloning the mutations $c_1$ and $c_2$, two fragment were amplified by primers YL-nsP3-PstI-F and YL-nsP4-OL-R from the plasmids L5-2 ($c_1$) and L5-4 ($c_2$), and by primers YL-nsP4-OL-F and YL-nsP4-AvrII-R from wild type replicon construct (ABC). Then the two fragments with the wild type replicon construct (ABC) digested by PstI-F and AvrII were assembled by NEBuilder® HiFi DNA Assembly kit. Other combinations were cloned in same method as above. The cited PCR primers are defined in Table 2.

To synthesize replicon constructs ABC-IL2-P2A-mCherry, $Ab_1C$-IL2-P2A-mCherry, and $Ab_1c_1$-IL2-P2A-mCherry, the fragments with BC (wild type), $b_1C$, and $b_1c_1$ were cut from the plasmids of VEE-ABC-mCherry, VEE-$Ab_1C$-mCherry, and VEE-$Ab_1c_1$-mCherry, respectively, by restriction enzymes EcoRI and PspXI. Then pYL026 were replaced by these fragments. All of the restriction enzymes were purchased from NEB.

To synthesize replicon constructs ABC-Luc, $Ab_1C$-Luc, and $Ab_1c_1$-Luc, the plasmids of ABC, $Ab_1C$, and $Ab_1c_1$ expressing mCherry were replaced with Luc fragment pBD059 (unpublished) between the restriction enzymes ApaI and SphI.

Antibodies, Flow Cytometry, Sorting, and Analysis

For analysis of CD8 T cells in B16F10 melanoma, single cell suspensions were prepared and stained[38] with fluorophore-conjugated antibodies against CD45 (Biolegend, Cat #103116, Clone 30-F11), CD8 (Biolegend, Cat #100706, Clone 53-6.7), and live dye Aqua (ThermoFisher Scientific, Cat #L34957). The stained cells were mixed with counting beads (ThermoFisher Scientific, Cat #C36950) and analyzed on a BD-LSRII Fortessa analyzer. All flow cytometry data were analyzed by FlowJo and the plots were prepared using GraphPad Prism.

RNA Extraction and Quantitative PCR Analysis

To quantify levels of RNA transcripts, total RNA was extracted from cells or tumors transfected with replicon RNA with the mutations as indicated and reverse transcribed by a TaqManÂ® Reverse Transcription Reagents Kit (ABI Catalog No. N8080234), followed by amplification with Sybr Green Master Mix (Roche) and specific primers YL-nsP3-qPCR-F and YL-nsP3-qPCR-R, YL-mCherry-F and YL-mCherry-R, YL-huActB-qPCR-F and YL-huActB-qPCR-R (Origene, Cat #HP204660), YL-mIL2-F and YL-mIL2-R (Origene, Cat #MP206769), and detected by a Roche LightCycler 480. The Ct values were normalized with housekeeping gene human Actin B for comparison.

Lipid Nanoparticle Formulation of Replicons for in Vivo Delivery

For encapsulating 10 μg replicon RNA, a lipid mixture composed of 16.9375 μl DOTAP (Avanti, Cat #890890, 10 mg/ml), 15.965 μl DSPC (Avanti, Cat #850365, 3 mg/ml), 18.7675 μl cholesterol (Sigma-Aldrich, Cat #C8667, 6 mg/ml), 13.6 μl DSPE-PEG2000 (Avanti Cat #880128, 2.5 mg/ml) in a molar ratio of 40:10:48:2 was prepared in ethanol and evaporated under $N_2$ till one third of the total initial volume remained. Then 10 μg replicon RNA (1 mg/ml) in 11.8 μl 0.1 M citrate buffer (PH 6.0) was added with pipetting, followed by a second addition of an additional 22 μl 0.1 M citrate buffer (PH 6.0) with pipetting. The mixture was shaken for an hour and then dialyzed against PBS for another hour at 25° C. in a 3,500 MWCO dialysis cassette. The resulting replicon-loaded lipid nanoparticles were aliquoted in appropriate dosages for intratumoral injection (10 μg/mouse) or for intramuscular injection (2.5 μg/mouse).

In Vivo Replicon Studies

For intratumoral injections, C57B1/6 mice were subcutaneously injected in the flank with $10^6$ B16F10 cells. Seven days post injection, melanoma tumors were intratumorally injected with 10 μg replicon RNA in lipid nanoparticles. Then tumor areas were measured at the days indicated with calipers or necropsied for flow cytometry or for total RNA extraction. To mimic vaccination, groups of C57B1/6 mice were intramuscularly injected with 2.5 μg lipid nanoparticle-formulated replicon RNA encoding luciferase. Then the mice were imaged using an In Vivo Imaging System (XENOGEN IVIS 200) at 10 minutes after subcutaneous injection of 200 μL luciferin (8 mg/mL in PBS, GoldBio Cat #LUCK-1G) near the melanoma tumor or the muscle injected with lipid nanoparticle-replicon.

Example 1

In Vitro Evolution of VEE Replicons to Identify Mutations Associated with Prolonged and Higher Payload Gene Expression In order to identify mutations in the replicon that impact the persistence and strength of expression of payload genes under the subgenomic promoter, an in vitro evolution strategy was designed using VEE replicons deleted of genes encoding the structural proteins, to focus the mutational screen on the nonstructural proteins involved in RNA replication and host machinery interactions. Although many replicon studies are carried out using BHK-21 cells that are deficient in interferon signaling, human Jurkat cells were employed here that have a functional interferon pathway for transfection and passage of replicons, in order to potentially select for mutations limiting the host cell interferon response. It was hypothesized that extended culture of replicon-transfected cells combined with repeated enrichment of highly-expressing cells would select for replicons bearing favorable mutations. VEE replicons expressing the fluorescent protein mCherry from the subgenomic region were synthesized by in vitro transcription (IVT) and transfected into Jurkat cells. Based on prior studies estimating RNA virus mutation rates,[39,40] the transfected cells were cultured for 60 days, sorting the top 20% of mCherry-expressing cells by flow cytometry approximately every 10 days. The percentage of $mCherry^{hi}$ cells and mean fluorescence intensity of mCherry expression increased with each sort (FIG. 1A), suggesting that mutations in either the replicon RNA or changes in the host Jurkat cells were favoring replicon persistence and stronger subgenome expression.

Figure 6A:
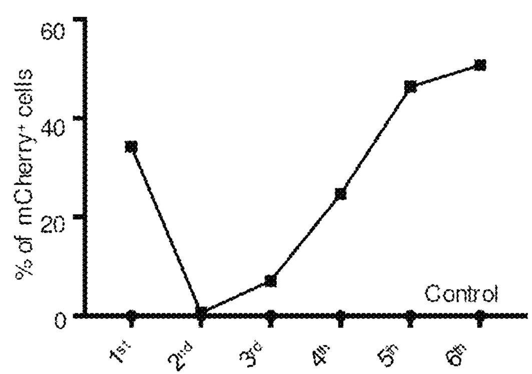
FIGS. 6A-6B. In vitro evolution increases mCherry expression from replicon RNA.
Figure 6B:
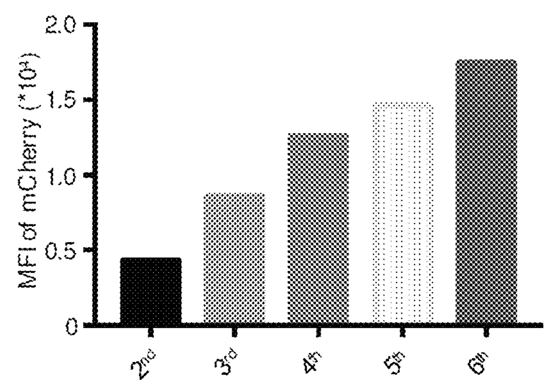

The percentage of mCherry-positive cells began to plateau after 6 sorts (FIGS. 6A-6B), and thus cells were selected from the $5^{th}$ sort for sequencing to assess potential mutations arising in the replicon. Total RNA was isolated from the sorted Jurkat cells isolated in this sort, reverse-transcribed to cDNA, and amplicons from seven overlapping regions covering the nonstructural proteins (loci L1-L7) were each separately cloned into plasmid vectors (FIG. 1B). Plasmids expressing the amplicon constructs were transfected into *E. coli*, and 6 colonies from each amplicon were isolated for Sanger sequencing. Each of the 7 amplified regions was treated as a genetic locus, and each clone bearing one or more mutations as an allele at that locus. Mutations were identified in 3 of the loci, L2, L4, and L5. The wild type alleles at each of these loci were named A, B, and C, respectively, while mutant alleles were assigned lowercase letters: A recovered amplicon sequence containing a synonymous point mutation in L2 was named allele a; two different mutant alleles identified in L4 were named $b_1$ and $b_2$; and two mutant alleles in L5 were named $c_1$ (bearing one point mutation) and $c_2$ (containing two point mutations) (FIG. 1C). Using this nomenclature, a replicon construct is specified by which alleles it bears at these three loci. The 3 WT (A, B, C) and 5 mutant alleles (a, $b_1$, $b_2$, $c_1$, $c_2$) from these 3 loci combine to give 18 total potential variants made up of unique WT/mutant allele combinations (Table 1). Replicon ABC, for example, is the wild-type replicon, while replicon $ab_2C$ has the mutant a allele at L2 and the mutant $b_2$ allele at L4, but the wild-type C allele at L5. As shown in FIG. 1B, the mutations were located in the D1/D2 and methyltransferase-like domains of nsP2 and the Macro and alphavirus unique domain (AUD) of nsP3.

Example 2

Figure 2B:
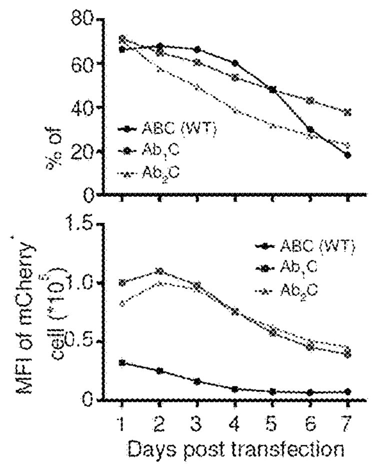

In Vitro-Selected Mutations Impact the Intensity and Longevity of Expression of Reporter Genes under the Subgenomic Promoter To better understand the impact of these mutations on gene expression from the replicon, 17 synthetic replicons were built using all combinations of the 5 mutant alleles identified in the screen (Table 1), and compared the strength and duration of transgene expression to the wild-type replicon (ABC). Each replicon was transfected into Jurkat cells and mCherry expression was tracked for 7 days using flow cytometry. Allele a had minimal impact on the proportion of cells expressing replicon or the level of subgenome expression (FIG. 2A). By contrast, alleles $b_1$ and $b_2$ increased the intensity of mCherry expression approximately 3-fold compared to the wild-type replicon (FIG. 2B). Alleles $c_1$ and $c_2$ alone elicited minor changes in expression relative to the WT replicon (FIG. 2C), but when $c_1$ was combined with allele $b_1$, the durability of mCherry expression over time was further enhanced (FIGS. 2D-2E). Summarizing the kinetic data in a plot of the day 1 mCherry mean fluorescence intensity vs. the rate of mCherry expression loss over time, the most improved replicons relative to the WT ABC sequence are readily identified, with mutants $Ab_1C$ and $Ab_1c_1$ showing particularly high levels of transgene expression combined with the lowest expression decay rates.

Example 3

Figure 3A:
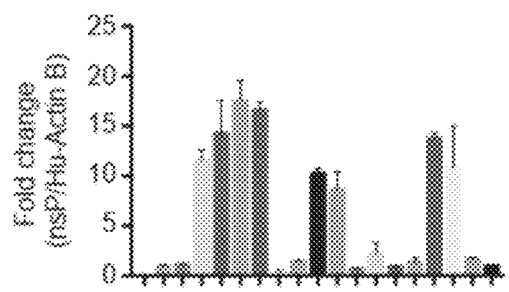
FIGS. 3A-3E. Alleles $b_1$ and $b_2$ enhance both subgenome and whole replicon genome RNA levels relative to WT replicons, while alleles $c_1$ and $c_2$ decrease subgenomic transcription. Jurkat cells were transfected with WT or mutant replicons and analyzed at day 5 for levels of nsP RNA (FIG. 3A, a surrogate for whole genome copies) or mCherry RNA (FIG. 3B) by qPCR. Shown are actin-normalized RNA levels relative to the WT ABC construct.
Figure 3B:
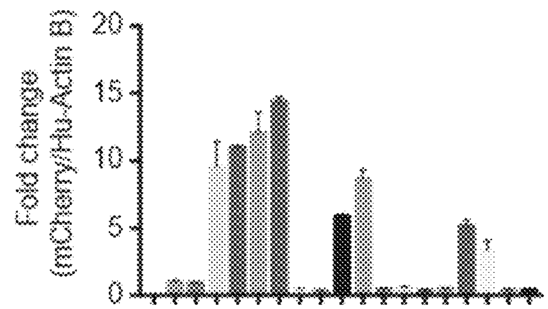

Alleles $b_1$ and $b_2$ Increase Replicon RNA Persistence, while $c_1$ and $c_2$ Decrease Subgenomic Transcription During alphavirus transcription by the nsPs, both copies of the entire replicon genome and shorter transcripts of only the subgenome are produced. Thus the impact of the replicon mutations on levels of intracellular subgenome vs. whole replicon genome transcripts was next evaluated. Relative levels of nonstructural proteins (FIG. 3A) and mCherry (FIG. 3B) transcripts in Jurkat cells transfected with all 18 replicons were measured by qPCR. Cells transfected with replicons $Ab_1C$, $ab_1C$, $Ab_2C$, $ab_2C$, $Ab_1c_1$, $ab_1c_2$, $Ab_1c_2$, and $ab_1c_2$ had 10-18 times more replicon RNA compared to cells transfected with the wild-type (ABC) replicon (FIG. 3A). Subgenomic RNA levels of mCherry RNA generally correlated with the nsP RNA levels. (FIG. 3B). Because alleles $b_1$ and $b_2$ at locus 4 demonstrated higher overall mCherry expression (FIG. 2A), this indicates that alleles $b_1$ and $b_2$ increase replicon RNA levels as well as mCherry subgenomic RNA level compared to the wild-type allele B, and that alleles $c_1$ and $c_2$ in Locus 5 suppress this effect in replicons with allele $b_2$ but not allele $b_1$.

Figure 3C:
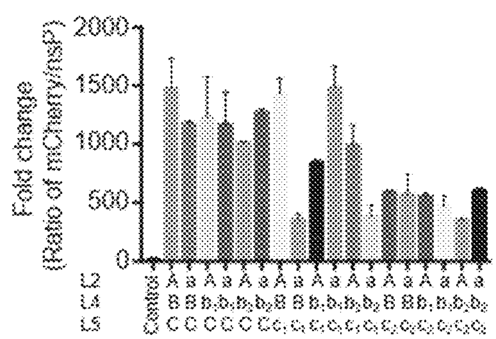

When comparing the level of mCherry transcripts to whole replicon genome RNA, constructs with allele C (the wild-type) at Locus 5 had ratios of 1000-1500. In contrast, replicons with allele $c_2$ demonstrated lower relative subgenome expression, with mCherry/nsP ratios of around 500. Replicons carrying allele $c_1$ had widely varying mCherry/nsP ratios, ranging from 500 to 1500, depending on the presence of other mutations (FIG. 3C). Taken together, these data suggest that alleles $b_1$ and $b_2$ (locus 4) increase levels of replicon RNA, while alleles $c_1$ and $c_2$ (locus 5) decrease subgenomic transcription. The effects of alleles $\alpha$ (locus 2) and $c_1$ (locus 5) are highly context-sensitive, depending on which alleles are at the other two loci.

Figure 2E:
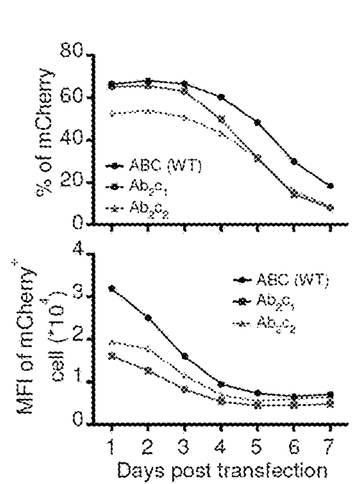
Figure 3D:
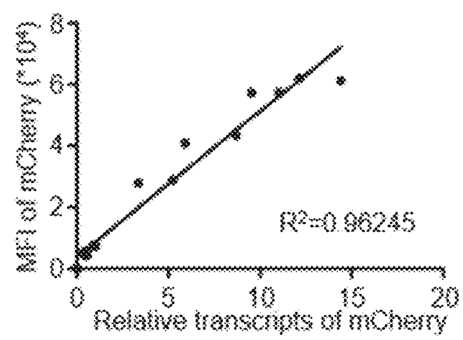
Figure 3E:
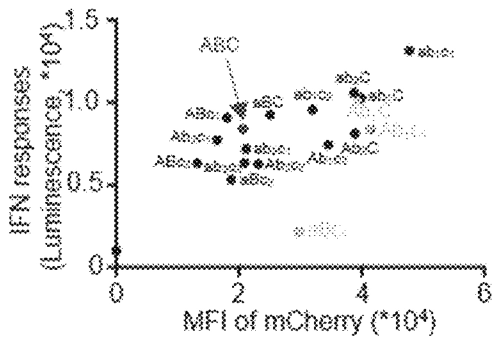
Figure 7:
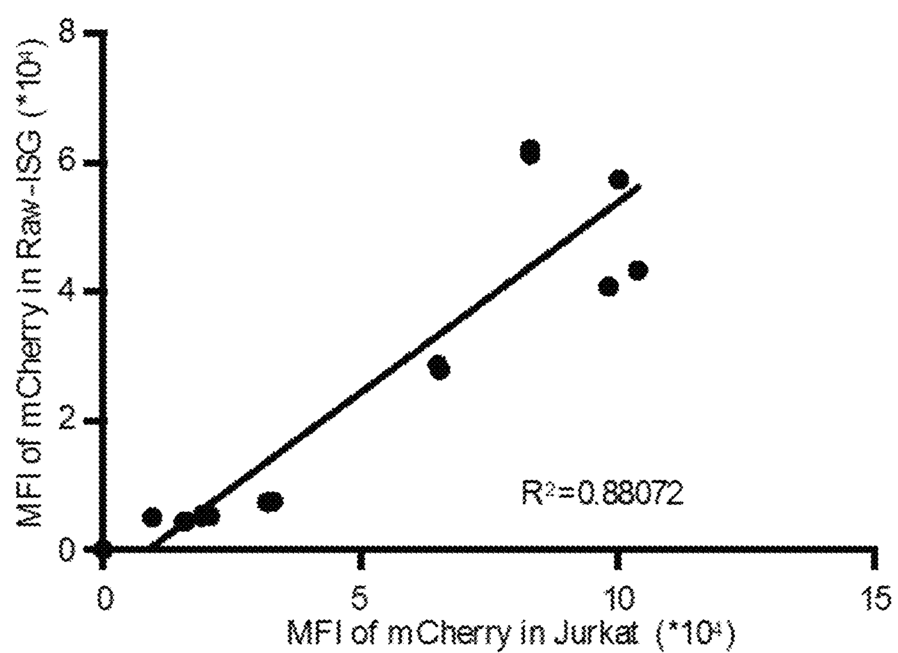
FIG. 7. Correlation between the MFI of mCherry in Jurkat and in RAW-ISG cells. Jurkat and RAW-ISG cells were transfected with WT or mutant replicons encoding mCherry as a reporter. MFI and the percentage of mCherry positive cells at day 1 post transfection were determined by flow cytometry. Coefficient of determination (R-squared) was indicated.

The mechanism that led to some mutant replicons being present in cells at levels 10 to 18-fold higher than wild type were of interest, because it was reasoned that these mutations may aid the replicon in escaping the cell's innate interferon response, which is activated by viral RNA and limits its replication.[19-21,23] To test this hypothesis, all 18 replicons were transfected into RAW-Lucia™ ISG cells, which secrete luciferase in response to interferon.[41,42] Levels of mCherry transcripts correlated with the MFI (mean fluorescence intensity) of mCherry (FIG. 3D), and the MFI of mCherry in the RAW-Lucia™ ISG cells showed similar trends as were observed in Jurkat cells (FIG. 7), suggesting that MFI of mCherry indicates the abundance of mCherry transcripts, and the replicon replication and expression dynamics are similar in these reporter cells. Thus, the IFN responses (Luminescence) versus the MFI of mCherry in RAW-Lucia™ ISG cells transfected with 18 replicons was compared (FIG. 3E). Five of six mutant replicons with allele $c_2$ showed lower IFN responses, suggesting the allele $c_2$ reduce IFN responses by restriction of subgenomic transcription (FIG. 3C). Similarly, 4 of 6 mutant replicons with allele $c_1$ decreased IFN responses, suggesting the allele $c_1$ is involved in escaping of IFN responses. Unexpectedly, 5 of 6 mutant replicons with allele $b_2$ also showed less IFN response, possibly because of the effects of low subgenomic expression by allele $b_2$ (FIG. 2E). In contrast, 4 of 6 mutant replicons with allele $b_1$ showed higher IFN responses, possibly because of the stimulation of IFN responses by more replicon RNA (FIG. 3A) as well as more subgenomic transcripts (FIG. 3B). The allele a, however, demonstrated more complicated effects on IFN responses, depending on presences of other alleles. Taken together, using Jurkat cells, several mutant alleles with altered interactions between the replicon and host cell's innate immune response were successfully screened out, though mechanisms underlying these changes may be complicated.

Figure 2C:
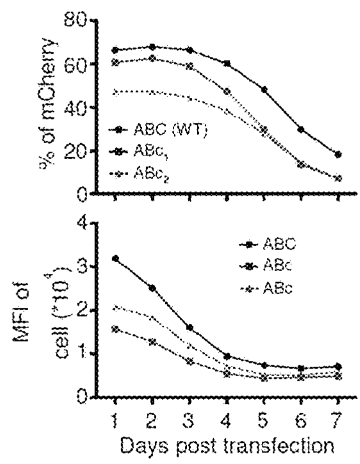
Figure 2D:
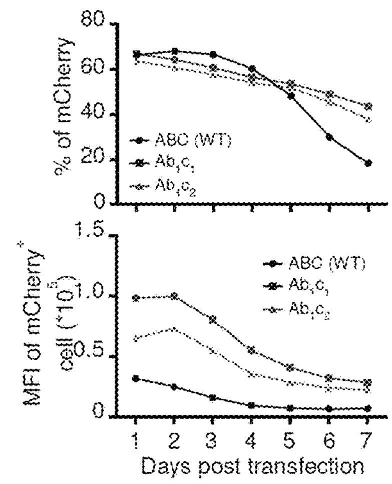
Figure 2F:
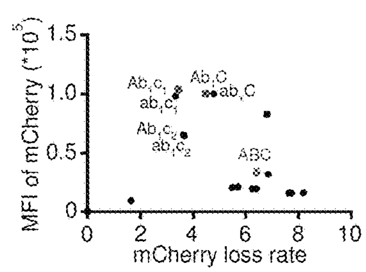

Interestingly, although mutants were found with a lower interferon response (e.g., $aBc_1$ and $aBc_2$), these replicons did not provide the best performance in terms of subgenome transgene expression (FIGS. 2C, 2F, and 3E).

The IVE screen identified 5 non-synonymous mutations associated with enhanced expression in Jurkat cells in vitro. Allele $b_1$ carried a favorable mutation in nsP2, a non-structural protein that has previously been shown to regulate the cytopathic effect of alphavirus infection.[28,29] The mutation in allele $b_2$ was located in the macrodomain of nsP3 but had similar effects on expression strength as allele $b_1$, consistent with prior art teaching that the protease and MTase domains in nsP2 and the macrodomain and AUD in nsP3 function as a compact complex.[43] Alleles $c_1$ and $c_2$ carried mutations in nsP3 which is involved in subgenomic transcription.[30] Herein, these alleles suppressed expression in combination with allele $b_2$ but enhanced the durability of expression when combined with allele $b_1$, suggesting that replicon transcription and subgenomic transcription are independent but related events.

In summary, five of the six mutations had a significant impact on replicon persistence and gene expression levels. Two mutations in nsP2 and nsP3 enhanced transgene expression, while mutations in nsP3 were identified that regulated this expression by suppressing subgenomic transcription. Interestingly, some of these mutations also altered the strength of the host cell's interferon response to the replicons.

Example 4

Mutant Replicons Increase Gene Expression Magnitude and Persistence in Vivo

Figure 4A:
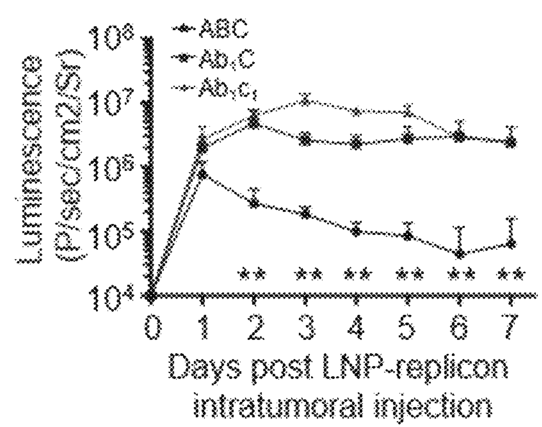
FIGS. 4A-4B. Replicon mutations impact the strength and persistence of transgene expression in vivo.
Figure 4B:
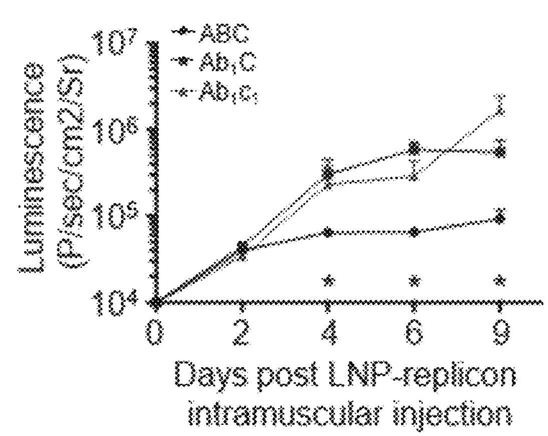

To evaluate the impact of evolved mutations on replicon expression in vivo, two of the mutant sequences with enhanced behavior in vitro were selected for further analysis and comparison to the wild type replicon: mutants $Ab_1C$ and $Ab_1c_1$ (highlighted in orange in FIGS. 2F and 3E) because these two mutants showed higher subgenomic expression, lower mCherry loss rate, and similar IFN responses, in comparison to wild type ABC. Mutant and wild type replicons encoding luciferase from the subgenome were synthesized and encapsulated in lipid nanoparticles designed for transfection in vivo.[12] Localized treatment of cancer using immunotherapeutics injected intratumorally is a therapy modality of growing interest clinically, based on preclinical and clinical evidence that locally-generated T cell responses can disseminate to cause regression of distal untreated tumors.[44-47] Modeling this setting, lipid nanoparticles carrying encapsulated replicon RNA were first injected intratumorally in C57BL/6J mice bearing B 16F10 melanoma tumors. While the WT VEE replicon showed steadily decaying expression from day 1 onward, both the $Ab_1C$ and $Ab_1c_1$ constructs maintained expression over the same time course, at a level ~10-fold greater on average than WT replicon (FIG. 4A). In a separate experiment, these three replicons were also injected intramuscularly to model their use in a vaccination setting. Intramuscular expression of all 3 replicons increased over time, but climbed substantially more rapidly for the mutant replicons, which exhibited on average ~6-fold greater bioluminescence signal by day 6 (FIG. 4B).

The in vivo results highlight the mutant replicons' therapeutic potential. Injected intramuscularly, a common site for vaccine administration, the mutant replicons showed more rapid and higher-level transgene expression over at least one week in vivo.

Example 5

Enhanced Anti-Tumor Immunity Stimulated by Mutant Replicons

Figure 5A:
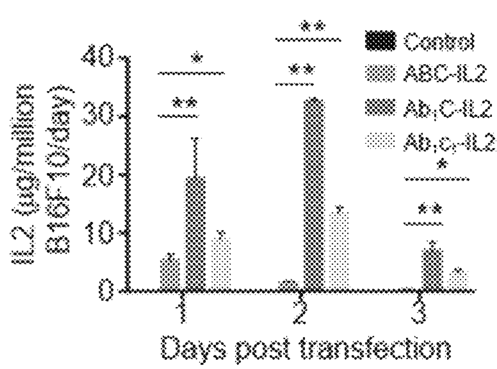
FIGS. 5A-5E. Mutant replicons encoding interleukin-2 exhibit enhanced gene expression and anti-tumor activity over WT VEE replicons.
Figure 5B:
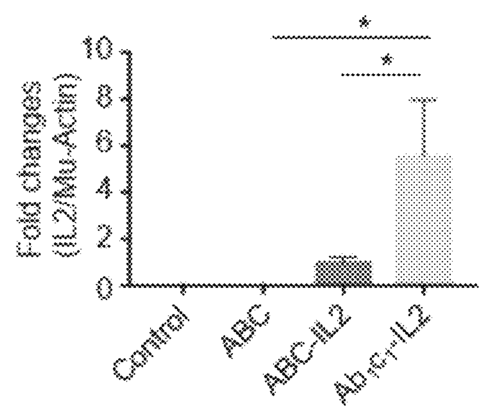
Figure 5C:
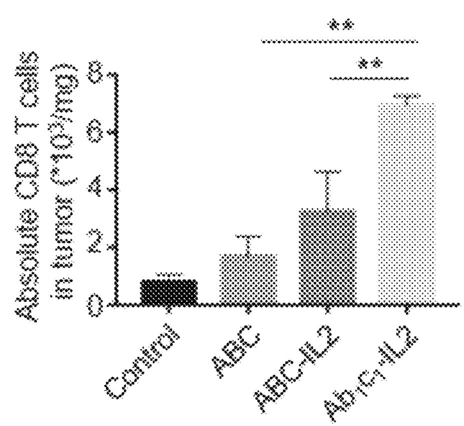
Figure 5D:
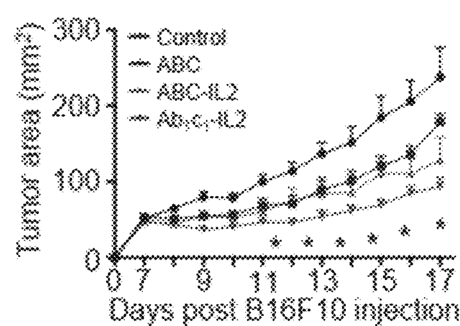
Figure 5E:
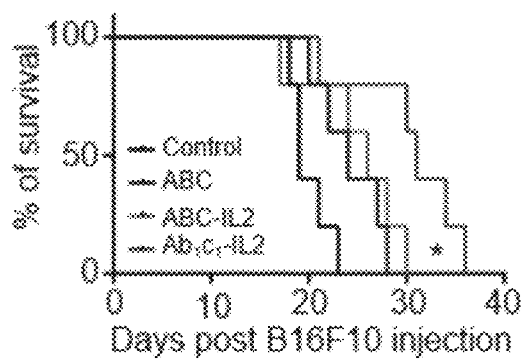

The enhanced expression of payload genes from the SGP of the mutant replicons suggest they could be an attractive platform for gene-based immunotherapy. As a preliminary exploration of this application, WT or mutant $Ab_1c_1$ replicons expressing interleukin-2 (IL-2) under the SGP were generated. IL-2 is a potent cytokine that promotes the proliferation and effector function of $CD8^+$ T cells and natural killer cells.[48] First, the secretion of IL-2 from transfected tumor cells in vitro was evaluated. As shown in FIG. 5A, even in vitro, replicon expression in B16F10 tumor cells transfected with WT replicon ABC encoding IL-2 decayed to near baseline by 48 hr., while secreted IL-2 protein was detected over at least 3 days in culture from the mutant replicons and at much higher levels than the WT construct. To assess replicon-based IL-2 expression in vivo, lipid nanoparticles carrying RNA were injected into established B 16F10 tumors, and IL-2 transcript levels were measured by PCR 3 days post injection. As shown in FIG. 5B, tumor samples injected with $Ab_1c_1$ replicons expressed 5.5-fold more transcripts than the WT replicon. Tumors with the $Ab_1c_1$ mutant replicon showed 2.1-fold more infiltrating CD8 T cells than the wild-type ABC replicon (FIG. 5C). A significant decrease in tumor growth was also observed (FIG. 5D) and improved survival (FIG. 5E) from the $Ab_1c_1$ mutant IL-2 expressing replicon compared to both the ABC IL-2 replicon, the ABC replicon without IL-2 and the vehicle control.

When applied in a model of cancer immunotherapy, replicons containing the most effective mutation combinations showed enhanced duration and level of cargo gene expression in vivo. When injected into murine B16F10 melanoma tumors, the optimal mutant replicons identified here encoding the immunoregulatory cytokine interleukin-2 significantly improved treatment of murine B16F10 melanoma through improved maintenance of CD8 T cells and significantly slowed tumor growth. Administered intratumorally, the best-performing mutant replicon showed strong transgene expression in vivo a week after administration, contrasting with rapid decay of expression from the wild type replicon. This increase in the strength and persistence of gene expression led to increased anti-tumor efficacy in a mouse melanoma model. Thus, implementation of this unique method of in vitro evolution allowed for the identification of therapeutically useful mutations and, when delivered in vivo, these mutant replicons may be useful for improved replicon-based RNA therapeutics for vaccination, cancer immunotherapy, and gene therapy. Further refinements in replicon design hold promise for controllable expression of antigens and immunomodulatory factors.

REFERENCES

1. Lächelt, U. & Wagner, E. Nucleic Acid Therapeutics Using Polyplexes: A Journey of 50 Years (and Beyond). *Chem. Rev.* 115, 11043-11078 (2015).
2. Prabakaran, S., Lippens, G., Steen, H. & Gunawardena, J. Post-translational modification: nature's escape from genetic imprisonment and the basis for dynamic information encoding. *Wiley Interdiscip. Rev. Syst. Biol. Med.* 4, 565-583 (2012).
3. Zavala-Cerna, M. G. et al. The Clinical Significance of Posttranslational Modification of Autoantigens. *Clin. Rev. Allergy Immunol.* 47, 73-90 (2014).
4. Guan, S. & Rosenecker, J. Nanotechnologies in delivery of mRNA therapeutics using nonviral vector-based delivery systems. *Gene Ther.* 24, 133-143 (2017).
5. Kaczmarek, J. C., Kowalski, P. S. & Anderson, D. G. Advances in the delivery of RNA therapeutics: from concept to clinical reality. *Genome Med.* 9, 60 (2017).
6. Karikó, K. et al. Incorporation of Pseudouridine Into mRNA Yields Superior Nonimmunogenic Vector With Increased Translational Capacity and Biological Stability. *Mol. Ther.* 16, 1833-1840 (2008).
7. Kuhn, A. N. et al. Phosphorothioate cap analogs increase stability and translational efficiency of RNA vaccines in immature dendritic cells and induce superior immune responses in vivo. *Gene Ther.* 17, 961-971 (2010).
8. Anderson, B. R. et al. Nucleoside modifications in RNA limit activation of 2'-5'-oligoadenylate synthetase and increase resistance to cleavage by RNase L. *Nucleic Acids Res.* 39, 9329-9338 (2011).
9. Youn, H. & Chung, J.-K. Modified mRNA as an alternative to plasmid DNA (pDNA) for transcript replacement and vaccination therapy. *Expert Opin. Biol. Ther.* 15, 1337-1348 (2015).
10. Schott, J. W., Morgan, M., Galla, M. & Schambach, A. Viral and Synthetic RNA Vector Technologies and Applications. *Mol. Ther.* 24, 1513-1527 (2016).
11. Lundstrom, K. Replicon RNA Viral Vectors as Vaccines. *Vaccines* 4, 39 (2016).
12. Geall, A. J. et al. Nonviral delivery of self-amplifying RNA vaccines. *Proc. Natl. Acad. Sci.* 109, 14604-14609 (2012).
13. Rodriguez-Madoz, J. R., Prieto, J. & Smerdou, C. Semliki Forest Virus Vectors Engineered to Express Higher IL-12 Levels Induce Efficient Elimination of Murine Colon Adenocarcinomas. *Mol. Ther.* 12, 153-163 (2005).
14. Ying, H. et al. Cancer therapy using a self-replicating RNA vaccine. *Nat. Med.* 5, 823-827 (1999).
15. Ramaswamy, S. et al. Systemic delivery of factor IX messenger RNA for protein replacement therapy. *Proc. Natl. Acad. Sci.* 114, E1941-E1950 (2017).
16. Beal, J. et al. Model-Driven Engineering of Gene Expression from RNA Replicons. *ACS Synth. Biol.* 4, 48-56 (2015).
17. Wroblewska, L. et al. Mammalian synthetic circuits with RNA binding proteins for RNA-only delivery. *Nat. Biotechnol.* 33, 839-841 (2015).
18. Pietschmann, T , Lohmann, V., Rutter, G., Kurpanek, K. & Bartenschlager, R. Characterization of Cell Lines Carrying Self-Replicating Hepatitis C Virus RNAs. *J. Virol.* 75, 1252-1264 (2001).
19. Naka, K. Interferon resistance of hepatitis C virus replicon-harbouring cells is caused by functional disruption of type I interferon receptors. *J. Gen. Virol.* 86, 2787-2792 (2005).
20. Guo, J. T., Bichko, V. V & Seeger, C. Effect of alpha interferon on the hepatitis C virus replicon. *J. Virol.* 75, 8516-23 (2001).
21. Jensen, S. & Thomsen, A. R. Sensing of RNA viruses: a review of innate immune receptors involved in recognizing RNA virus invasion. *J. Virol.* 86, 2900-10 (2012).
22. Duportet, X. et al. A platform for rapid prototyping of synthetic gene networks in mammalian cells. *Nucleic Acids Res.* 42, 13440-51 (2014).
23. Frolova, E. I. et al. Roles of nonstructural protein nsP2 and Alpha/Beta interferons in determining the outcome of Sindbis virus infection. *J. Virol.* 76, 11254-64 (2002).
24. Gelderblom, H. R. *Structure and Classification of Viruses. Medical Microbiology* (University of Texas Medical Branch at Galveston, 1996).
25. Uversky, V. N., Longhi, S. & Wiley InterScience (Online service). *Flexible viruses: structural disorder in viral proteins*. (Wiley, 2012).
26. Strauss, J. H. & Strauss, E. G. The alphaviruses: gene expression, replication, and evolution. *Microbiol. Rev.* 58, 491-562 (1994).
27. Kinney, R. M. et al. Attenuation of Venezuelan equine encephalitis virus strain TC-83 is encoded by the 5'-noncoding region and the E2 envelope glycoprotein. *J. Virol.* 67, 1269-77 (1993).
28. Garmashova, N., Gorchakov, R., Frolova, E. & Frolov, I. Sindbis virus nonstructural protein nsP2 is cytotoxic and inhibits cellular transcription. *J. Virol.* 80, 5686-96 (2006).
29. Mayuri, Geders, T. W., Smith, J. L. & Kuhn, R. J. Role for conserved residues of sindbis virus nonstructural protein 2 methyltransferase-like domain in regulation of minus-strand synthesis and development of cytopathic infection. *J. Virol.* 82, 7284-97 (2008).
30. LaStarza, M. W., Lemm, J. A. & Rice, C. M. Genetic analysis of the nsP3 region of Sindbis virus: evidence for roles in minus-strand and subgenomic RNA synthesis. *J. Virol.* 68, 5781-91 (1994).
31. Temin, H. M. Function of the retrovirus long terminal repeat. *Cell* 28, 3-5 (1982).
32. MacDonald, M. R., Machlin, E. S., Albin, O. R. & Levy, D. E. The zinc finger antiviral protein acts synergistically with an interferon-induced factor for maximal activity against alphaviruses. *J. Virol.* 81, 13509-18 (2007).
33. Merly, L. & Smith, S. L. Murine RAW 264.7 cell line as an immune target: are we missing something? *Immunopharmacol. Immunotoxicol.* 39, 55-58 (2017).
34. Griffiths, A. J. F. *Modern genetic analysis*. (W. H. Freeman, 1999).
35. Puri, A. et al. Lipid-based nanoparticles as pharmaceutical drug carriers: from concepts to clinic. *Crit. Rev. Ther. Drug Carrier Syst.* 26, 523-80 (2009).
36. Davis, N. L., Willis, L. V, Smith, J. F. & Johnston, R. E. In vitro synthesis of infectious venezuelan equine encephalitis virus RNA from a cDNA clone: analysis of a viable deletion mutant. Virology 171, 189-204 (1989).

37. Yoshioka, N. et al. Efficient Generation of Human iPSCs by a Synthetic Self-Replicative RNA. *Cell Stem Cell* 13, 246-254 (2013).

38. Li, Y. et al. Persistent Antigen and Prolonged AKT-mTORC1 Activation Underlie Memory CD8 T Cell Impairment in the Absence of CD4 T Cells. *J. Immunol.* 195, 1591-8 (2015).

39. Sanjuan, R., Nebot, M. R., Chirico, N., Mansky, L. M. & Belshaw, R. Viral Mutation Rates. *J. Virol.* 84, 9733-9748 (2010).

40. Drake, J. W. Rates of spontaneous mutation among RNA viruses. *Proc. Natl. Acad. Sci. U.S.A.* 90, 4171-5 (1993).

41. Kawasaki, T., Kawai, T. & Akira, S. Recognition of nucleic acids by pattern-recognition receptors and its relevance in autoimmunity. Immunol. Rev. 243, 61-73 (2011).

42. Stein, S. C. & Falck-Pedersen, E. Sensing adenovirus infection: activation of interferon regulatory factor 3 in RAW 264.7 cells. *J. Virol.* 86, 4527-37 (2012).

43. Shin, G. et al. Structural and functional insights into alphavirus polyprotein processing and pathogenesis. *Proc. Natl. Acad. Sci. U.S.A.* 109, 16534-9 (2012).

44. Kwong, B., Gai, S. A., Elkhader, J., Wittrup, K. D. & Irvine, D. J. Localized Immunotherapy via Liposome-Anchored Anti-CD137+IL-2 Prevents Lethal Toxicity and Elicits Local and Systemic Antitumor Immunity. *Cancer Res.* 73, 1547-1558 (2013).

45. Aznar, M. A. et al. Intratumoral Delivery of Immunotherapy—Act Locally, Think Globally. *J. Immunol.* 198, 31-39 (2017).

46. Marabelle, A., Kohrt, H., Caux, C. & Levy, R. Intratumoral Immunization: A New Paradigm for Cancer Therapy. *Clin. Cancer Res.* 20, 1747-1756 (2014).

47. van den Boom, J. G. & Hartmann, G. Turning Tumors into Vaccines: Co-opting the Innate Immune System. *Immunity* 39, 27-37 (2013).

48. Boyman, O. & Sprent, J. The role of interleukin-2 during homeostasis and activation of the immune system. *Nat. Rev. Immunol.* 12, 180-190 (2012).

Sequence Listing (SEQ ID NOs: 1-18)

>ABC (AEH)

SEQ ID NO: 1

```
ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA
```

-continued

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

-continued

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG -continued CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>aBC (BEH)

SEQ ID NO: 2

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

-continued

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

-continued

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

-continued

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab1C (ADH)

SEQ ID NO: 3

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

-continued

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

-continued

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

-continued

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

-continued

>ab1C (BDH)

SEQ ID NO: 4

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

-continued

```
CTGGCATAGACATGACCACTGAACAATGGAACACTGTGGATTATTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA
```

-continued

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

-continued

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab2C (ACH)

SEQ ID NO: 5

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

-continued

```
TCTGCGGGGATCCCAAACAGTGCGGTTTTTTTAACATGATGTGCCTGAAAGTGCATTTTAACCACGAGATTTGCACACAAG
TCTTCCACAAAAGCATCTCTCGCCGTTGCACTAAATCTGTGACTTCGGTCGTCTCAACCTTGTTTTACGACAAAAAAATGAG
AACGACGAATCCGAAAGAGACTAAGATTGTGATTGACACTACCGGCAGTACCAAACCTAAGCAGGACGATCTCATTCTCA
CTTGTTTCAGAGGGTGGGTGAAGCAGTTGCAAATAGATTACAAAGGCAACGAAATAATGACGGCAGCTGCCTCTCAAGG
GCTGACCCGTAAAGGTGTGTATGCCGTTCGGTACAAGGTGAATGAAAATCCTCTGTACGCACCCACCTCAGAACATGTGA
ACGTCCTACTGACCCGCACGGAGGACCGCATCGTGTGGAAAACACTAGCCGGCGACCCATGGATAAAAACACTGACTGC
CAAGTACCCTGGGAATTTCACTGCCACGATAGAGGAGTGGCAAGCAGAGCATGATGCCATCATGAGGCACATCTTGGAG
AGACCGGACCCTACCGACGTCTTCCAGAATAAGGCAAACGTGTGTTGGGCCAAGGCTTTAGTGCCGGTGCTGAAGACCG
CTGGCATAGACATGACCACTGAACAATGGAACACTGTGGATTATTTTGAAACGGACAAAGCTCACTCAGCAGAGATAGTA
TTGAACCAACTATGCGTGAGGTTCTTTGGACTCGATCTGGACTCCGGTCTATTTTCTGCACCCACTGTTCCGTTATCCATTA
GGAATAATCACTGGGATAACTCCCCGTCGCCTAACATGTACGGGCTGAATAAAGAAGTGGTCCGTCAGCTCTCTCGCAGG
TACCCACAACTGCCTCGGGCAGTTGCCACTGGAAGAGTCTATGACATGAACACTGGTACACTGCGCAATTATGATCCGCG
CATAAACCTAGTACCTGTAAACAGAAGACTGCCTCATGCTTTAGTCCTCCACCATAATGAACACCCACAGAGTGACTTTTCT
TCATTCGTCAGCAAATTGAAGGGCAGAACTGTCCTGGTGGTCGGGGAAAAGTTGTCCGTCCCAGGCAAAATGGTTGACTG
GTTGTCAGACCGGCCTGAGGCTACCTTCAGAGCTCGGCTGGATTTAGGCATCCCAGGTGATGTGCCCAAATATGACATAA
TATTTGTTAATGTGAGGACCCCATATAAATACCATCACTATCAGCAGTGTGAAGACCATGCCATTAAGCTTAGCATGTTGA
CCAAGAAAGCTTGTCTGCATCTGAATCCCGGCGGAACCTGTGTCAGCATAGGTTATGGTTACGCTGACAGGGCCAGCGAA
AGCATCATTGGTGCTATAGCGCGGCAGTTCAAGTTTTCCCGGGTATGCAAACCGAAATCCTCACTTGAAGAGACGGAAGT
TCTGTTTGTATTCATTGGGTACGATCGCAAGGCCCGTACGCACAATTCTTACAAGCTTTCATCAACCTTGACCAACATTTAT
ACAGGTTCCAGACTCCACGAAGCCGGATGTGCACCCTCATATCATGTGGTGCGAGGGGATATTGCCACGGCCACCGAAG
GAGTGATTATAAATGCTGCTAACAGCAAAGGACAACCTGGCGGAGGGGTGTGCGGAGCGCTGTATAAGAAATTCCCGGA
AAGCTTCGATTTACAGCCGATCGAAGTAGGAAAAGCGCGACTGGTCAAAGGTGCAGCTAAACATATCATTCATGCCGTAG
GACCAAACTTCAACAAAGTTTCGGAGGTTGAAGGTGACAAACAGTTGGCAGAGGCTTATGAGTCCATCGCTGAGATTGTC
AACGATAACAATTACAAGTCAGTAGCGATTCCACTGTTGTCCACCGGCATCTTTTCCGGGAACAAAGATCGACTAACCCAA
TCATTGAACCATTTGCTGACAGCTTTAGACACCACTGATGCAGATGTAGCCATATACTGCAGGGACAAGAAATGGGAAAT
GACTCTCAAGGAAGCAGTGGCTAGGAGAGAAGCAGTGGAGGAGATATGCATATCCGACGACTCTTCAGTGACAGAACCT
GATGCAGAGCTGGTGAGGGTGCATCCGAAGAGTTCTTTGGCTGGAAGGAAGGGCTACAGCACAAGCGATGGCAAAACT
TTCTCATATTTGGAAGGGACCAAGTTTCACCAGGCGGCCAAGGATATAGCAGAAATTAATGCCATGTGGCCCGTTGCAAC
GGAGGCCAATGAGCAGGTATGCATGTATATCCTCGGAGAAAGCATGAGCAGTATTAGGTCGAAATGCCCCGTCGAAGAG
TCGGAAGCCTCCACACCACCTAGCACGCTGCCTTGCTTGTGCATCCATGCCATGACTCCAGAAAGAGTACAGCGCCTAAAA
GCCTCACGTCCAGAACAAATTACTGTGTGCTCATCCTTTCCATTGCCGAAGTATAGAATCACTGGTGTGCAGAAGATCCAA
TGCTCCCAGCCTATATTGTTCTCACCGAAAGTGCCTGCGTATATTCATCCAAGGAAGTATCTCGTGGAAACACCACCGGTA
GACGAGACTCCGGAGCCATCGGCAGAGAACCAATCCACAGAGGGGACACCTGAACAACCACCACTTATAACCGAGGATG
AGACCAGGACTAGAACGCCTGAGCCGATCATCATCGAAGAGGAAGAAGAGGATAGCATAAGTTTGCTGTCAGATGGCCC
GACCCACCAGGTGCTGCAAGTCGAGGCAGACATTCACGGGCCGCCCTCTGTATCTAGCTCATCCTGGTCCATTCCTCATGC
ATCCGACTTTGATGTGGACAGTTTATCCATACTTGACACCCTGGAGGGAGCTAGCGTGACCAGCGGGGCAACGTCAGCCG
AGACTAACTCTTACTTCGCAAAGAGTATGGAGTTTCTGGCGCGACCGGTGCCTGCGCCTCGAACAGTATTCAGGAACCCTC
CACATCCCGCTCCGCGCACAAGAACACCGTCACTTGCACCCAGCAGGGCCTGCTCGAGAACCAGCCTAGTTTCCACCCCGC
CAGGCGTGAATAGGGTGATCACTAGAGAGGAGCTCGAGGCGCTTACCCCGTCACGCACTCCTAGCAGGTCGGTCTCGAG
AACCAGCCTGGTCTCCAACCCGCCAGGCGTAAATAGGGTGATTACAAGAGAGGAGTTTGAGGCGTTCGTAGCACAACAA
```

-continued

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

-continued

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>ab2C (BCH)

SEQ ID NO: 6

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

-continued

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTGAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

-continued

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

-continued

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>ABc1 (AEF)

SEQ ID NO: 7

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

-continued

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

-continued

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg -continued ccaccATGGTGAGCAAGGGCGAGGAGGATAACATGGCCATCATCAAGGAGTTCATGCGCTTCAAGGTGCACATGGAGGGCTC
CGTGAACGGCCACGAGTTCGAGATCGAGGGCGAGGGCGAGGGCCGCCCCTACGAGGGCACCCAGACCGCCAAGCTGAAGGT
GACCAAGGGTGGCCCCCTGCCCTTCGCCTGGGACATCCTGTCCCCTCAGTTCATGTACGGCTCCAAGGCCTACGTGAAGCA
CCCCGCCGACATCCCCGACTACTTGAAGCTGTCCTTCCCCGAGGGCTTCAAGTGGGAGCGCGTGATGAACTTCGAGGACG
GCGGCGTGGTGACCGTGACCCAGGACTCCTCCCTGCAGGACGGCGAGTTCATCTACAAGGTGAAGCTGCGCGGCACCAA
CTTCCCCTCCGACGGCCCCGTAATGCAGAAGAAGACCATGGGCTGGGAGGCCTCCTCCGAGCGGATGTACCCCGAGGAC
GGCGCCCTGAAGGGCGAGATCAAGCAGAGGCTGAAGCTGAAGGACGGCGGCCACTACGACGCTGAGGTCAAGACCACC
TACAAGGCCAAGAAGCCCGTGCAGCTGCCCGGCGCCTACAACGTCAACATCAAGTTGGACATCACCTCCCACAACGAGGA
CTACACCATCGTGGAACAGTACGAACGCGCCGAGGGCCGCCACTCCACCGGCGGCATGGACGAGCTGTACAAGTAGgaat
tGGCAAGCTGCTTACATAGAACTCGCGGCGATTGGCATGCCGCCTTAAAATTTTTATTTTATTTTTCTTTTCTTTTCCGAAT
CGGATTTTGTTTTTAATATTTCAAAAAAAAAAAAAAAAAAAAAAAAAAACGCGTCGAGGGGAATTAATTCTTGAAGACGAAA
GGGCCAGGTGGCACTTTTCGGGGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTGGTGAAAGTAAAAGATGCTGAAGATC
AGTTGGGTGCACGAGTGGGTTACATCGAACTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCCCGTGTTGACGCCGGGCAAGAGCAACTCGGT
CGCCGCATACACTATTCTCAGAATGACTTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAACCGGAGCTGAATGAAGCCA
TACCAAACGACGAGCGTGACACCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACTATGGATGAACGAAATAGACAGATCGCTG
AGATAGGTGCCTCACTGATTAAGCATTGGTAACTGTCAGACCAAGTTTACTCATATATACTTTAGATTGATTTAAAACTTCA
TTTTTAATTTAAAAGGATCTAGGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGAGCGAACGACCTACA
CCGAACTGAGATACCTACAGCGTGAGCATTGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCTATGGAAAAACGCCAGCAACG
CGAGCTCTAATACGACTCACTATAG >aBc1 (BEF)

SEQ ID NO: 8

ATGGGCGGCGCATGAGAGAAGCCCAGACCAATTACCTACCCAAAATGGAGAAAGTTCACGTTGACATCGAGGAAGACAG
CCCATTCCTCAGAGCTTTGCAGCGGAGCTTCCCGCAGTTTGAGGTAGAAGCCAAGCAGGTCACTGATAATGACCATGCTA
ATGCCAGAGCGTTTTCGCATCTGGCTTCAAAACTGATCGAAACGGAGGTGGACCCATCCGACACGATCCTTGACATTGGA
AGTGCGCCCGCCCGCAGAATGTATTCTAAGCACAAGTATCATTGTATCTGTCCGATGAGATGTGCGGAAGATCCGGACAG
ATTGTATAAGTATGCAACTAAGCTGAAGAAAAACTGTAAGGAAATAACTGATAAGGAATTGGACAAGAAAATGAAGGAG

-continued

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGBGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

-continued

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

-continued

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

-continued

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab1c1 (ADF)

SEQ ID NO: 9

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

-continued

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

-continued

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

-continued

AGATAGGTGCCTCACTGATTAAGCATTGGTAACTGTCAGACCAAGTTTACTCATATATACTTTAGATTGATTTAAAACTTCA
TTTTTAATTTAAAAGGATCTAGGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCGAAGGTAACTGGCTTCAGCA
GAGCGCAGATACCAAATACTGTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTACCGGGTTGGACTCAAGACGAT
AGTTACCGGATAAGGCGCAGCGGTCGGGCTGAACGGGGGGTTCGTGCACACAGCCCAGCTTGGAGCGAACGACCTACA
CCGAACTGAGATACCTACAGCGTGAGCATTGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCTATGGAAAAACGCCAGCAACG
CGAGCTCTAATACGACTCACTATAG

>ab1c1 (BDF)

SEQ ID NO: 10

ATGGGCGGCGCATGAGAGAAGCCCAGACCAATTACCTACCCAAAATGGAGAAAGTTCACGTTGACATCGAGGAAGACAG
CCCATTCCTCAGAGCTTTGCAGCGGAGCTTCCCGCAGTTTGAGGTAGAAGCCAAGCAGGTCACTGATAATGACCATGCTA
ATGCCAGAGCGTTTTCGCATCTGGCTTCAAAACTGATCGAAACGGAGGTGGACCCATCCGACACGATCCTTGACATTGGA
AGTGCGCCCGCCCGCAGAATGTATTCTAAGCACAAGTATCATTGTATCTGTCCGATGAGATGTGCGGAAGATCCGGACAG
ATTGTATAAGTATGCAACTAAGCTGAAGAAAAACTGTAAGGAAATAACTGATAAGGAATTGGACAAGAAAATGAAGGAG
CTGGCCGCCGTCATGAGCGACCCTGACCTGGAAACTGAGACTATGTGCCTCCACGACGACGAGTCGTGTCGCTACGAAGG
GCAAGTCGCTGTTTACCAGGATGTATACGCGGTTGACGGACCGACAAGTCTCTATCACCAAGCCAATAAGGGAGTTAGAG
TCGCCTACTGGATAGGCTTTGACACCACCCCTTTTATGTTTAAGAACTTGGCTGGAGCATATCCATCATACTCTACCAACTG
GGCCGACGAAACCGTGTTAACGGCTCGTAACATAGGCCTATGCAGCTCTGACGTTATGGAGCGGTCACGTAGAGGGATG
TCCATTCTTAGAAAGAAGTATTTGAAACCATCCAACAATGTTCTATTCTCTGTTGGCTCGACCATCTACCACGAGAAGAGG
GACTTACTGAGGAGCTGGCACCTGCCGTCTGTATTTCACTTACGTGGCAAGCAAAATTACACATGTCGGTGTGAGACTATA
GTTAGTTGCGACGGGTACGTCGTTAAAAGAATAGCTATCAGTCCAGGCCTGTATGGGAAGCCTTCAGGCTATGCTGCTAC
GATGCACCGCGAGGGATTCTTGTGCTGCAAAGTGACAGACACATTGAACGGGGAGAGGGTCTCTTTTCCCGTGTGCACGT
ATGTGCCAGCTACATTGTGTGACCAAATGACTGGCATACTGGCAACAGATGTCAGTGCGGACGACGCGCAAAAACTGCTG
GTTGGGCTCAACCAGCGTATAGTCGTCAACGGTCGCACCCAGAGAAACACCAATACCATGAAAAATTACCTTTTGCCCGTA
GTGGCCCAGGCATTTGCTAGGTGGGCAAAGGAATATAAGGAAGATCAAGAAGATGAAAGGCCACTAGGACTACGAGAT
AGACAGTTAGTCATGGGGTGTTGTTGGGCTTTTAGAAGGCACAAGATAACATCTATTTATAAGCGCCCGGATACCCAAAC
CATCATCAAAGTGAACAGCGATTTCCACTCATTCGTGCTGCCCAGGATAGGCAGTAACACATTGGAGATCGGGCTGAGAA
CAAGAATCAGGAAAATGTTAGAGGAGCACAAGGAGCCGTCACCTCTCATTACCGCCGAGGACGTACAAGAAGCTAAGTG
CGCAGCCGATGAGGCTAAGGAGGTGCGTGAAGCCGAGGAGTTGCGCGCAGCTCTACCACCTTTGGCAGCTGATGTTGAG
GAGCCCACTCTGGAGGCAGACGTCGACTTGATGTTACAAGAGGCTGGGGCCGGCTCAGTGGAGACACCTCGTGGCTTGA
TAAAGGTTACCAGCTACGATGGCGAGGACAAGATCGGCTCTTACGCTGTGCTTTCTCCGCAGGCTGTACTCAAGAGTGAA
AAATTATCTTGCATCCACCCTCTCGCTGAACAAGTCATAGTGATAACACACTCTGGCCGAAAAGGGCGTTATGCCGTGGAA
CCATACCATGGTAAAGTAGTGGTGCCAGAGGGACATGCAATACCCGTCCAGGACTTTCAAGCTCTGAGTGAAAGTGCCAC
CATTGTGTACAACGAACGTGAGTTCGTAAACAGGTACCTGCACCATATTGCCACACATGGGGGAGCGCTGAACACTGATG
AAGAATATTACAAAACTGTCAAGCCCAGCGAGCACGACGGCGAATACCTGTACGACATCGACAGGAAACAGTGCGTCAA
GAAAGAACTAGTCACTGGGCTAGGGCTCACAGGCGAGCTGGTGGATCCTCCCTTCCATGAATTCGCCTACGAGAGTCTGA
GAACACGACCAGCCGCTCCTTACCAAGTACCAACCATAGGGGTGTATGGCGTGCCAGGATCAGGCAAGTCTGGCATCATT
AAAAGCGCAGTCACCAAAAAAGATCTAGTGGTGAGCGCCAAGAAAGAAAACTGTGCAGAAATTATAAGGGACGTCAAG

-continued

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

-continued

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

-continued

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab2c1 (ACF)

SEQ ID NO: 11

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

-continued

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTGAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

-continued

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

-continued

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>ab2c1 (BCF)

SEQ ID NO: 12

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

-continued

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTGAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAGGCATGAGCAGTATTAGGTCGAAATGCCCCGTCGAAGAG

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTGTGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

-continued

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>ABc2 (AEG)

SEQ ID NO: 13

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

-continued

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

-continued

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

-continued

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

-continued

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>aBc2 (BEG)

SEQ ID NO: 14

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

-continued

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

-continued

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab1c2 (ADG)

SEQ ID NO: 15

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

-continued

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

-continued

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC -continued CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>ab1c2 (BDG)

SEQ ID NO: 16

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

-continued

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTCGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTAAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

>Ab2c2 (ACG)

SEQ ID NO: 17

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

-continued

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGAGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

-continued

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTGAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

-continued

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

-continued

>ab2c2 (BCG)

SEQ ID NO: 18

ATGGGCGGCGCATGAGAGAAGCCCAGACCAATTACCTACCCAAAATGGAGAAAGTTCACGTTGACATCGAGGAAGACAG

CCCATTCCTCAGAGCTTTGCAGCGGAGCTTCCCGCAGTTTGAGGTAGAAGCCAAGCAGGTCACTGATAATGACCATGCTA

ATGCCAGAGCGTTTTCGCATCTGGCTTCAAAACTGATCGAAACGGAGGTGGACCCATCCGACACGATCCTTGACATTGGA

AGTGCGCCCGCCCGCAGAATGTATTCTAAGCACAAGTATCATTGTATCTGTCCGATGAGATGTGCGGAAGATCCGGACAG

ATTGTATAAGTATGCAACTAAGCTGAAGAAAAACTGTAAGGAAATAACTGATAAGGAATTGGACAAGAAAATGAAGGAG

CTGGCCGCCGTCATGAGCGACCCTGACCTGGAAACTGAGACTATGTGCCTCCACGACGACGAGTCGTGTCGCTACGAAGG

GCAAGTCGCTGTTTACCAGGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATATCCATCATACTCTACCAACTG

GGCCGACGAAACCGTGTTAACGGCTCGTAACATAGGCCTATGCAGCTCTGACGTTATGGAGCGGTCACGTAGAGGGATG

TCCATTCTTAGAAAGAAGTATTTGAAACCATCCAACAATGTTCTATTCTCTGTTGGCTCGACCATCTACCACGAGAAGAGG

GACTTACTGAGGAGCTGGCACCTGCCGTCTGTATTTCACTTACGTGGCAAGCAAAATTACACATGTCGGTGTGAGACTATA

GTTAGTTGCGACGGGTACGTCGTTAAAAGAATAGCTATCAGTCCAGGCCTGTATGGGAAGCCTTCAGGCTATGCTGCTAC

GATGCACCGCGAGGGATTCTTGTGCTGCAAAGTGACAGACACATTGAACGGGGAGAGGGTCTCTTTTCCCGTGTGCACGT

ATGTGCCAGCTACATTGTGTGACCAAATGACTGGCATACTGGCAACAGATGTCAGTGCGGACGACGCGCAAAAACTGCTG

GTTGGGCTCAACCAGCGTATAGTCGTCAACGGTCGCACCCAGAGAAACACCAATACCATGAAAAATTACCTTTTGCCCGTA

GTGGCCCAGGCATTTGCTAGGTGGGCAAAGGAATATAAGGAAGATCAAGAAGATGAAAGGCCACTAGGACTACGAGAT

AGACAGTTAGTCATGGGGTGTTGTTGGGCTTTTAGAAGGCACAAGATAACATCTATTTATAAGCGCCCGGATACCCAAAC

CATCATCAAAGTGAACAGCGATTTCCACTCATTCGTGCTGCCCAGGATAGGCAGTAACACATTGGAGATCGGGCTGAGAA

CAAGAATCAGGAAAATGTTAGAGGAGCACAAGGAGCCGTCACCTCTCATTACCGCCGAGGACGTACAAGAAGCTAAGTG

CGCAGCCGATGAGGCTAAGGAGGTGCGTGAAGCCGAGGAGTTGCGCGCAGCTCTACCACCTTTGGCAGCTGATGTTGAG

GAGCCCACTCTGGAGGCAGACGTCGACTTGATGTTACAAGAGGCTGGGGCCGGCTCAGTGGAGACACCTCGTGGCTTGA

TAAAGGTTACCAGCTACGATGGCGAGGACAAGATCGGCTCTTACGCTGTGCTTTCTCCGCAGGCTGTACTCAAGAGTGAA

AAATTATCTTGCATCCACCCTCTCGCTGAACAAGTCATAGTGATAACACACTCTGGCCGAAAAGGGCGTTATGCCGTGGAA

CCATACCATGGTAAAGTAGTGGTGCCAGAGGGACATGCAATACCCGTCCAGGACTTTCAAGCTCTGAGTGAAAGTGCCAC

CATTGTGTACAACGAACGTGAGTTCGTAAACAGGTACCTGCACCATATTGCCACACATGGGGGAGCGCTGAACACTGATG

AAGAATATTACAAAACTGTCAAGCCCAGCGAGCACGACGGCGAATACCTGTACGACATCGACAGGAAACAGTGCGTCAA

GAAAGAACTAGTCACTGGGCTAGGGCTCACAGGCGAGCTGGTGGATCCTCCCTTCCATGAATTCGCCTACGAGAGTCTGA

GAACACGACCAGCCGCTCCTTACCAAGTACCAACCATAGGGGTGTATGGCGTGCCAGGATCAGGCAAGTCTGGCATCATT

AAAAGCGCAGTCACCAAAAAAGATCTAGTGGTGAGCGCCAAGAAAGAAAACTGTGCAGAAATTATAAGGGACGTCAAG

AAAATGAAAGGGCTGGACGTCAATGCCAGAACTGTGGACTCAGTGCTCTTGAATGGATGCAAACACCCCGTAGAGACCC

TGTATATTGACGAAGCTTTTGCTTGTCATGCAGGTACTCTCAGAGCGCTCATAGCCATTATAAGACCTAAAAAGGCAGTGC

TCTGCGGGGATCCCAAACAGTGCGGTTTTTTAACATGATGTGCCTGAAAGTGCATTTTAACCACGAGATTTGCACACAAG

TCTTCCACAAAAGCATCTCTCGCCGTTGCACTAAATCTGTGACTTCGGTCGTCTCAACCTTGTTTTACGACAAAAAAATGAG

AACGACGAATCCGAAAGAGACTAAGATTGTGATTGACACTACCGGCAGTACCAAACCTAAGCAGGACGATCTCATTCTCA

CTTGTTTCAGAGGGTGGGTGAAGCAGTTGCAAATAGATTACAAAGGCAACGAAATAATGACGGCAGCTGCCTCTCAAGG

GCTGACCCGTAAAGGTGTGTATGCCGTTCGGTACAAGGTGAATGAAAATCCTCTGTACGCACCCACCTCAGAACATGTGA

ACGTCCTACTGACCCGCACGGAGGACCGCATCGTGTGGAAAACACTAGCCGGCGACCCATGGATAAAAACACTGACTGC

CAAGTACCCTGGGAATTTCACTGCCACGATAGAGGAGTGGCAAGCAGAGCATGATGCCATCATGAGGCACATCTTGGAG

AGACCGGACCCTACCGACGTCTTCCAGAATAAGGCAAACGTGTGTTGGGCCAAGGCTTTAGTGCCGGTGCTGAAGACCG

-continued

CTGGCATAGACATGACCACTGAACAATGGAACACTGTGGATTATTTTGAAACGGACAAAGCTCACTCAGCAGAGATAGTA

TTGAACCAACTATGCGTGAGGTTCTTTGGACTCGATCTGGACTCCGGTCTATTTTCTGCACCCACTGTTCCGTTATCCATTA

GGAATAATCACTGGGATAACTCCCCGTCGCCTAACATGTACGGGCTGAATAAAGAAGTGGTCCGTCAGCTCTCTCGCAGG

TACCCACAACTGCCTCGGGCAGTTGCCACTGGAAGAGTCTATGACATGAACACTGGTACACTGCGCAATTATGATCCGCG

CATAAACCTAGTACCTGTAAACAGAAGACTGCCTCATGCTTTAGTCCTCCACCATAATGAACACCCACAGAGTGACTTTTCT

TCATTCGTCAGCAAATTGAAGGGCAGAACTGTCCTGGTGGTCGGGGAAAAGTTGTCCGTCCCAGGCAAAATGGTTGACTG

GTTGTCAGACCGGCCTGAGGCTACCTTCAGAGCTCGGCTGGATTTAGGCATCCCAGGTGATGTGCCCAAATATGACATAA

TATTTGTTAATGTGAGGACCCCATATAAATACCATCACTATCAGCAGTGTGAAGACCATGCCATTAAGCTTAGCATGTTGA

CCAAGAAAGCTTGTCTGCATCTGAATCCCGGCGGAACCTGTGTCAGCATAGGTTATGGTTACGCTGACAGGGCCAGCGAA

AGCATCATTGGTGCTATAGCGCGGCAGTTCAAGTTTTCCCGGGTATGCAAACCGAAATCCTCACTTGAAGAGACGGAAGT

TCTGTTTGTATTCATTGGGTACGATCGCAAGGCCCGTACGCACAATTCTTACAAGCTTTCATCAACCTTGACCAACATTTAT

ACAGGTTCCAGACTCCACGAAGCCGGATGTGCACCCTCATATCATGTGGTGCGAGGGGATATTGCCACGGCCACCGAAG

GAGTGATTATAAATGCTGCTAACAGCAAAGGACAACCTGGCGGAGGGGTGTGCGGAGCGCTGTATAAGAAATTCCCGGA

AAGCTTCGATTTACAGCCGATCGAAGTAGGAAAAGCGCGACTGGTCAAAGGTGCAGCTAAACATATCATTCATGCCGTAG

GACCAAACTTCAACAAAGTTTCGGAGGTTGAAGGTGACAAACAGTTGGCAGAGGCTTATGAGTCCATCGCTGAGATTGTC

AACGATAACAATTACAAGTCAGTAGCGATTCCACTGTTGTCCACCGGCATCTTTTCCGGGAACAAAGATCGACTAACCCAA

TCATTGAACCATTTGCTGACAGCTTTAGACACCACTGATGCAGATGTAGCCATATACTGCAGGGACAAGAAATGGGAAAT

GACTCTCAAGGAAGCAGTGGCTAGGAGAGAAGCAGTGGAGGAGATATGCATATCCGACGACTCTTCAGTGACAGAACCT

GATGCAGAGCTGGTGAGGGTGCATCCGAAGAGTTCTTTGGCTGGAAGGAAGGGCTACAGCACAAGCGATGGCAAAACT

TTCTCATATTTGGAAGGGACCAAGTTTCACCAGGCGGCCAAGGATATAGCAGAAATTAATGCCATGTGGCCCGTTGCAAC

GGAGGCCAATGAGCAGGTATGCATGTATATCCTCGGAGAAAGCATGAGCAGTATTAGGTCGAAATGCCCCGTCGAAGAT

TCGGAAGCCTCCACACCACCTAGCACGCTGCCTTGCTTGTGCATCCATGCCATGACTCCAGAAAGAGTACAGCGCCTAAAA

GCCTCACGTCCAGAACAAATTACTGTGTGCTCATCCTTTCCATTGCCGAAGTATAGAATCACTGGTATGCAGAAGATCCAA

TGCTCCCAGCCTATATTGTTCTCACCGAAAGTGCCTGCGTATATTCATCCAAGGAAGTATCTCGTGGAAACACCACCGGTA

GACGAGACTCCGGAGCCATCGGCAGAGAACCAATCCACAGAGGGGACACCTGAACAACCACCACTTATAACCGAGGATG

AGACCAGGACTAGAACGCCTGAGCCGATCATCATCGAAGAGGAAGAAGAGGATAGCATAAGTTTGCTGTCAGATGGCCC

GACCCACCAGGTGCTGCAAGTCGAGGCAGACATTCACGGGCCGCCCTCTGTATCTAGCTCATCCTGGTCCATTCCTCATGC

ATCCGACTTTGATGTGGACAGTTTATCCATACTTGACACCCTGGAGGGAGCTAGCGTGACCAGCGGGGCAACGTCAGCCG

AGACTAACTCTTACTTCGCAAAGAGTATGGAGTTTCTGGCGCGACCGGTGCCTGCGCCTCGAACAGTATTCAGGAACCCTC

CACATCCCGCTCCGCGCACAAGAACACCGTCACTTGCACCCAGCAGGGCCTGCTCGAGAACCAGCCTAGTTTCCACCCCGC

CAGGCGTGAATAGGGTGATCACTAGAGAGGAGCTCGAGGCGCTTACCCCGTCACGCACTCCTAGCAGGTCGGTCTCGAG

AACCAGCCTGGTCTCCAACCCGCCAGGCGTAAATAGGGTGATTACAAGAGAGGAGTTTGAGGCGTTCGTAGCACAACAA

CAATGACGGTTTGATGCGGGTGCATACATCTTTTCCTCCGACACCGGTCAAGGGCATTTACAACAAAAATCAGTAAGGCA

AACGGTGCTATCCGAAGTGGTGTTGGAGAGGACCGAATTGGAGATTTCGTATGCCCCGCGCCTCGACCAAGAAAAAGAA

GAATTACTACGCAAGAAATTACAGTTAAATCCCACACCTGCTAACAGAAGCAGATACCAGTCCAGGAAGGTGGAGAACAT

GAAAGCCATAACAGCTAGACGTATTCTGCAAGGCCTAGGGCATTATTTGAAGGCAGAAGGAAAAGTGGAGTGCTACCGA

ACCCTGCATCCTGTTCCTTTGTATTCATCTAGTGTGAACCGTGCCTTTTCAAGCCCCAAGGTCGCAGTGGAAGCCTGTAACG

CCATGTTGAAAGAGAACTTTCCGACTGTGGCTTCTTACTGTATTATTCCAGAGTACGATGCCTATTTGGACATGGTTGACG

GAGCTTCATGCTGCTTAGACACTGCCAGTTTTTGCCCTGCAAAGCTGCGCAGCTTTCCAAAGAAACACTCCTATTTGGAAC

CCACAATACGATCGGCAGTGCCTTCAGCGATCCAGAACACGCTCCAGAACGTCCTGGCAGCTGCCACAAAAAGAAATTGC

AATGTCACGCAAATGAGAGAATTGCCCGTATTGGATTCGGCGGCCTTTAATGTGGAATGCTTCAAGAAATATGCGTGTAA

TAATGAATATTGGGAAACGTTTAAAGAAAACCCCATCAGGCTTACTGAAGAAAACGTGGTAAATTACATTACCAAATTAA

AAGGACCAAAAGCTGCTGCTCTTTTTGCGAAGACACATAATTTGAATATGTTGCAGGACATACCAATGGACAGGTTTGTA

ATGGACTTAAAGAGAGACGTGAAAGTGACTCCAGGAACAAAACATACTGAAGAACGGCCCAAGGTACAGGTGATCCAG

GCTGCCGATCCGCTAGCAACAGCGTATCTGTGCGGAATCCACCGAGAGCTGGTTAGGAGATTAAATGCGGTCCTGCTTCC

GAACATTCATACACTGTTTGATATGTCGGCTGAAGACTTTGACGCTATTATAGCCGAGCACTTCCAGCCTGGGGATTGTGT

TCTGGAAACTGACATCGCGTCGTTTGATAAAAGTGAGGACGACGCCATGGCTCTGACCGCGTTAATGATTCTGGAAGACT

TAGGTGTGGACGCAGAGCTGTTGACGCTGATTGAGGCGGCTTTCGGCGAAATTTCATCAATACATTTGCCCACTAAAACT

AAATTTAAATTCGGAGCCATGATGAAATCTGGAATGTTCCTCACACTGTTTGTGAACACAGTCATTAACATTGTAATCGCA

AGCAGAGTGTTGAGAGAACGGCTAACCGGATCACCATGTGCAGCATTCATTGGAGATGACAATATCGTGAAAGGAGTCA

AATCGGACAAATTAATGGCAGACAGGTGCGCCACCTGGTTGAATATGGAAGTCAAGATTATAGATGCTGTGGTGGGCGA

GAAAGCGCCTTATTTCTGTGGAGGGTTTATTTTGTGTGACTCCGTGACCGGCACAGCGTGCCGTGTGGCAGACCCCCTAA

AAAGGCTGTTTAAGCTTGGCAAACCTCTGGCAGCAGACGATGAACATGATGATGACAGGAGAAGGGCATTGCATGAAGA

GTCAACACGCTGGAACCGAGTGGGTATTCTTTCAGAGCTGTGCAAGGCAGTAGAATCAAGGTATGAAACCGTAGGAACT

TCCATCATAGTTATGGCCATGACTACTCTAGCTAGCAGTGTTAAATCATTCAGCTACCTGAGAGGGGCCCCTATAACTCTCT

ACGGCTAACCTGAATGGACTACGACATAGTCTAGTCCGCCAAGTCTAGcatatgggcgcgccctcagcatcgattgaattgg ccaccATGGTGAGCAAGGGCGAGGAGGATAACATGGCCATCATCAAGGAGTTCATGCGCTTCAAGGTGCACATGGAGGGCTC CGTGAACGGCCACGAGTTCGAGATCGAGGGCGAGGGCGAGGGCCGCCCCTACGAGGGCACCCAGACCGCCAAGCTGAAGGT GACCAAGGGTGGCCCCCTGCCCTTCGCCTGGGACATCCTGTCCCCTCAGTTCATGTACGGCTCCAAGGCCTACGTGAAGCA

CCCCGCCGACATCCCCGACTACTTGAAGCTGTCCTTCCCCGAGGGCTTCAAGTGGGAGCGCGTGATGAACTTCGAGGACG

GCGGCGTGGTGACCGTGACCCAGGACTCCTCCCTGCAGGACGGCGAGTTCATCTACAAGGTGAAGCTGCGCGGCACCAA

CTTCCCCTCCGACGGCCCCGTAATGCAGAAGAAGACCATGGGCTGGGAGGCCTCCTCCGAGCGGATGTACCCCGAGGAC

GGCGCCCTGAAGGGCGAGATCAAGCAGAGGCTGAAGCTGAAGGACGGCGGCCACTACGACGCTGAGGTCAAGACCACC

TACAAGGCCAAGAAGCCCGTGCAGCTGCCCGGCGCCTACAACGTCAACATCAAGTTGGACATCACCTCCCACAACGAGGA

CTACACCATCGTGGAACAGTACGAACGCGCCGAGGGCCGCCACTCCACCGGCGGCATGGACGAGCTGTACAAGTAGgaat tGGCAAGCTGCTTACATAGAACTCGCGGCGATTGGCATGCCGCCTTAAAATTTTTATTTTATTTTTCTTTTCTTTTCCGAAT CGGATTTTGTTTTTAATATTTCAAAAAAAAAAAAAAAAAAAAAAAAAAAAACGCGTCGAGGGGAATTAATTCTTGAAGACGAAA GGGCCAGGTGGCACTTTTCGGGGAAATGTGCGCGGAACCCCTATTTGTTTATTTTTCTAAATACATTCAAATATGTATCCG CTCATGAGACAATAACCCTGATAAATGCTTCAATAATATTGAAAAAGGAAGAGTATGAGTATTCAACATTTCCGTGTCGCC CTTATTCCCTTTTTTGCGGCATTTTGCCTTCCTGTTTTTGCTCACCCAGAAACGCTGGTGAAAGTAAAAGATGCTGAAGATC

AGTTGGGTGCACGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAAGAGCAACTCGGT

CGCCGCATACACTATTCTCAGAATGACTTGGTTGAGTACTCACCAGTCACAGAAAAGCATCTTACGGATGGCATGACAGTA

AGAGAATTATGCAGTGCTGCCATAACCATGAGTGATAACACTGCGGCCAACTTACTTCTGACAACGATCGGAGGACCGAA

GGAGCTAACCGCTTTTTTGCACAACATGGGGGATCATGTAACTCGCCTTGATCGTTGGGAACCGGAGCTGAATGAAGCCA

TACCAAACGACGAGCGTGACACCACGATGCCTGTAGCAATGGCAACAACGTTGCGCAAACTATTAACTGGCGAACTACTT

ACTCTAGCTTCCCGGCAACAATTAATAGACTGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAACTATGGATGAACGAAATAGACAGATCGCTG

AGATAGGTGCCTCACTGATTAAGCATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATCCCTTAACGTGAGTTTTCGTTCCAC

-continued

TGAGCGTCAGACCCCGTAGAAAAGATCAAAGGATCTTCTTGAGATCCTTTTTTTCTGCGCGTAATCTGCTGCTTGCAAACAA

AAAAACCACCGCTACCAGCGGTGGTTTGTTTGCCGGATCAAGAGCTACCAACTCTTTTTCCGAAGGTAACTGGCTTCAGCA

GAGCGCAGATACCAAATACTGTCCTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTTACCGGGTTGGACTCAAGACGAT

AGTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCATTGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGTATCTTTATAGTCCTGTCGG

GTTTCGCCACCTCTGACTTGAGCGTCGATTTTTGTGATGCTCGTCAGGGGGGCGGAGCCTATGGAAAAACGCCAGCAACG

CGAGCTCTAATACGACTCACTATAG

TABLE 1

Description of wild type alleles and mutant alleles as well as all combinations of these alleles. Locus 2 has wild type allele A, and mutant allele a. Locus 4 has wild type allele B, mutant allele $b_1$ and $b_2$. Locus 5 has wild type allele C, mutant allele $c_1$ and $c_2$. Mutant allele $c_2$ has two linked mutations. The nucleotide and amino acid changes of mutant alleles are indicated. The localizations of mutant alleles at nsP are also illustrated. All 18 combinations (SEQ ID NOs: 1-18) of these independent 8 alleles are shown to the right of the vertical line.

| Information | | | | | Combination | | | | | | | |
|---|---|---|---|---|---|---|---|---|---|---|---|---|
| Locus | Allele | nucleotide | AA | region | ABC | aBC | $Ab_1C$ | $ab_1C$ | $Ab_2C$ | $ab_2C$ | $ABc_1$ | $aBc_1$ |
| L2 | A | | | | A | | A | | A | | A | |
| | a | A1979G | G656G | nsP2 | | a | | a | | a | | a |
| L4 | B | | | | B | B | | | | | B | B |
| | $b_1$ | G3936C | G1309R | nsP2 | | | $b_1$ | $b_1$ | | | | |
| | $b_2$ | A4311G | K143E | nsP3 | | | | | $b_2$ | $b_2$ | | |
| L5 | C | | | | C | C | C | C | C | C | | |
| | $c_1$ | A4758G | S1583G | nsP3 | | | | | | | $c_1$ | $c_1$ |
| | $c_2$ | G4796T/ G4944A | E1595D/ V1645M | nsP3 | | | | | A | | A | |

| | Combination | | | | | | | | | | |
|---|---|---|---|---|---|---|---|---|---|---|---|
| | ABC | $Ab_1c_1$ | $ab_1c_1$ | $Ab_2c_1$ | $ab_2c_1$ | $ABc_2$ | $aBc_2$ | $Ab_1c_2$ | $ab_1c_2$ | $Ab_2c_2$ | $ab_2c_2$ |
| | A | A | | A | | A | | A | | A | |
| | | | a | | a | | a | | a | | a |
| | B | | | | | B | B | | | | |
| | | $b_1$ | $b_1$ | | | | | $b_1$ | $b_1$ | | |
| | | | | $b_2$ | $b_2$ | | | | | $b_2$ | $b_2$ |
| | C | | | | | | | | | | |
| | | $c_1$ | $c_1$ | $c_1$ | $c_1$ | | | | | | |
| | | | | | | $c_2$ | $c_2$ | $c_2$ | $c_2$ | $c_2$ | $c_2$ |

TABLE 2

Sequences for the PCR primers used to amplify seven overlapping loci regions (locus 1-locus 7), which were defined on the nsPl-nsP4 regions and subgenomic promoter region.

| Primers | Sequences | SEQ ID NO |
|---|---|---|
| YL-mCherry-Clal-F | ATGGGCGCGCCCTCAGCATCGATTGAATTGGCCACCATGGT-GAGCAAGGGCGAGGA | 19 |
| YL-mCherry-R1 | TCGCCGCGAGTTCTATGTAAGCAGCTTGCCAATTCCTACTTGTACAGCTCGTCCA | 20 |
| YL-mCherry-Sphl-R2 | AAATAAAATAAAAATTTTAAGGCGGCATGCCAATCGCCGCGAGTTCTATGTAA | 21 |
| YL-locus-5'UTR-F1 | TATTGGGCGCTCTTCCGCTGGTCTCACACCATGGGCGGCGCATGAGAGAA | 22 |

TABLE 2-continued

Sequences for the PCR primers used to amplify seven overlapping loci regions (locus 1-locus 7), which were defined on the nsP1-nsP4 regions and subgenomic promoter region.

| Primers | Sequences | SEQ ID NO |
|---|---|---|
| YL-locus-R1 | TCAGTGAGCGAGGAAGCGGTCTCATTATACGACTATACGCTGGTTGAG | 23 |
| YL-locus-F2 | TATTGGGCGCTCTTCCGCTGGTCTCACACCTGGCAACAGATGTCAGTGCG | 24 |
| YL-locus-R2 | TCAGTGAGCGAGGAAGCGGTCTCATTATAATGATGCCAGACTTGCCTG | 25 |
| YL-locus-F3 | TATTGGGCGCTCTTCCGCTGGTCTCACACCTACCAAGTACCAACCATAGG | 26 |
| YL-locus-R3 | TCAGTGAGCGAGGAAGCGGTCTCATTATTTCAGCCCGTACATGTTAGG | 27 |
| YL-locus-F4 | TATTGGGCGCTCTTCCGCTGGTCTCACACCTAATCACTGGGATAACTCCC | 28 |
| YL-locus-R4 | TCAGTGAGCGAGGAAGCGGTCTCATTATCATCTGCATCAGTGGTGTCT | 29 |
| YL-locus-F5 | TATTGGGCGCTCTTCCGCTGGTCTCACACCTTGAACCATTTGCTGACAGC | 30 |
| YL-locus-R5 | TCAGTGAGCGAGGAAGCGGTCTCATTATTCCTCTCTAGTGATCACCCT | 31 |
| YL-locus-F6 | TATTGGGCGCTCTTCCGCTGGTCTCACACCAGAACCAGCCTAGTTTCCAC | 32 |
| YL-locus-R6 | TCAGTGAGCGAGGAAGCGGTCTCATTATAACCAGCTCTCGGTGGATTC | 33 |
| YL-locus-F7 | TATTGGGCGCTCTTCCGCTGGTCTCACACCGCTAGCAACAGCGTATCTGT | 34 |
| YL-locus-R7 | TCAGTGAGCGAGGAAGCGGTCTCATTATATGGCCATGTTATCCTCCTC | 35 |
| YL-nsP2-Xmal-F | GCGCGGCTGTTCAAGTTTTC | 36 |
| YL-nsP3-Pstl-R | TTTCCCATTTCTTGTCCCTGCAGTATATGGCTACATCTGCATCAGTGGTGTCT | 37 |
| YL-nsP3-Pstl-F | ATGCAGATGTAGCCATATAC | 38 |
| YL-nsP4-OL-R | GATCACCCTATTCACGCCTG | 39 |
| YL-nsP4-OL-F | CAGGCGTGAATAGGGTGATC | 40 |
| YL-nsP4-Avrll-R | CTTCTGCCTTCAAATAATGC | 41 |
| YL-nsP2-Bsal-F | TATTGGGCGCTCTTCCGCTGGTCTCACACCAGCATAGGTTATGGTTACGC | 42 |
| YL-nsP3-Bsal-R | TCAGTGAGCGAGGAAGCGGTCTCATTATTACGCAGGCACTTTCGGTGA | 43 |
| YL-nsP3-qPCR-F | ATGCCGTAGGACCAAACTTC | 44 |
| YL-nsP3-qPCR-R | TGGTGTCTAAAGCTGTCAGC | 45 |
| YL-mCherry-F | CTTCAAGGTGCACATGGAGG | 46 |
| YL-mCherry-R | AGGACAGCTTCAAGTAGTCG | 47 |
| YL-hActB-qPCR-F | CACCATTGGCAATGAGCGGTTC | 48 |
| YL-hActB-qPCR-R | AGGTCTTTGCGGATGTCCACGT | 49 |
| YL-mlL2-F | GCGGCATGTTCTGGATTTGACTC | 50 |
| YL-mlL2-R | CCACCACAGTTGCTGACTCATC | 51 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS AND SCOPE

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nucleic acid molecule comprising a nucleotide sequence as shown in any one of SEQ ID NOs: 1-18, or any combination of two or more of SEQ ID NOs: 1-18.

2. A nucleic acid molecule comprising a portion of a nucleotide sequence as shown in any one of SEQ ID NOs: 1-18, or any combination of two or more portions of SEQ ID NOs: 1-18, wherein the portion of the nucleotide sequence comprises a combination of two or more mutations relative to the corresponding wild-type Venezuelan equine encephalitis (VEE) virus ribonucleic acid (RNA) selected from the group consisting of A1979G, G3936C, A4311G, A4758G, G4796T, and G4944A, wherein the position of the mutation (s) is relative to SEQ ID NO: 1.

3. An alphavirus replicon comprising the nucleic acid molecule of claim 2.

4. The replicon of claim 3, wherein the replicon encodes non-structural proteins for replication, but does not encode structural proteins for viral formation.

5. The replicon of claim 3, wherein the replicon comprises the untranslated regions, non-structural proteins, and subgenomic promoter of the alphavirus.

6. The replicon of claim 3, wherein the structural proteins of the replicon are replaced by one or more gene(s) of experimental or therapeutic interest.

7. The replicon of claim 6, wherein the one or more gene(s) of experimental or therapeutic interest encodes Interleukin-2 (IL-2) or luciferase.

8. The replicon of claim 3, wherein the replicon is engineered to express a detectable molecule in the subgenomic region of the replicon.

9. The replicon of claim 8, wherein the detectable molecule is a fluorescent protein.

10. The nucleic acid molecule of claim 2, wherein the portion of the nucleotide sequence is at least 50, 100, 200, 300, 400, 500, 600, 700, 800, 900, or 1000 nucleotides in length.

11. The replicon of claim 6, wherein the one or more gene(s) encode cytokines, chemokines, or growth factors.

12. The replicon of claim 8, wherein the detectable molecule is a nucleic acid or polypeptide.

13. The replicon of claim 9, wherein the fluorescent protein is mCherry, mKate, blue fluorescent protein, yellow fluorescent protein, red fluorescent protein, mVenus, green fluorescent protein, mRaspberry, or mStrawberry.

14. An alphavirus replicon comprising the nucleic acid molecule of claim 1.

15. The replicon of claim 14, wherein the replicon encodes non-structural proteins for replication, but does not encode structural proteins for viral formation.

16. The replicon of claim 15, wherein the structural proteins of the alphavirus replicon are replaced by one or more gene(s) of experimental or therapeutic interest.

17. The replicon of claim 16, wherein the one or more gene(s) of experimental or therapeutic interest encodes Interleukin-2 (IL-2) or luciferase.

18. The replicon of claim 15, wherein the alphavirus replicon is engineered to express a detectable molecule in the subgenomic region of the replicon.

19. The replicon of claim 18, wherein the detectable molecule is a nucleic acid or polypeptide.

20. The replicon of claim 18, wherein the detectable molecule is a fluorescent protein.

* * * * *

SEQUENCE LISTING

<160> NUMBER OF SEQ ID NOS: 51

<210> SEQ ID NO 1
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 1
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300

```
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
```

```
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
```

```
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
```

```
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
```

```
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                 10276
```

```
<210> SEQ ID NO 2
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 2
```

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
```

```
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatgggg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataaggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg actttctttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
```

```
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
```

```
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
```

```
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                 10276
```

```
<210> SEQ ID NO 3
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 3
```

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
```

```
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
```

```
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
```

```
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
```

```
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
```

```
tagcaccgcc tacatacctc gctctgctaa tcctgttacc agtggctgct gccagtggcg   9900

ataagtcgtg tcttaccggg ttggactcaa gacgatagtt accggataag gcgcagcggt   9960

cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276


<210> SEQ ID NO 4
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 4

atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaggcagacg   1620
```

```
tcgacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800

taacacactc tggccgaaaa gggcgttatg ccgtggaacc ataccatggt aaagtagtgg   1860

tgccagaggg acatgcaata cccgtccagg actttcaagc tctgagtgaa agtgccacca   1920

ttgtgtacaa cgaacgtgag ttcgtaaaca ggtacctgca ccatattgcc acacatgggg   1980

gagcgctgaa cactgatgaa gaatattaca aaactgtcaa gcccagcgag cacgacggcg   2040

aatacctgta cgacatcgac aggaaacagt gcgtcaagaa agaactagtc actgggctag   2100

ggctcacagg cgagctggtg gatcctccct tccatgaatt cgcctacgag agtctgagaa   2160

cacgaccagc cgctccttac caagtaccaa ccataggggt gtatggcgtg ccaggatcag   2220

gcaagtctgg catcattaaa agcgcagtca ccaaaaaaga tctagtggtg agcgccaaga   2280

aagaaaactg tgcagaaatt ataagggacg tcaagaaaat gaaagggctg gacgtcaatg   2340

ccagaactgt ggactcagtg ctcttgaatg gatgcaaaca ccccgtagag accctgtata   2400

ttgacgaagc ttttgcttgt catgcaggta ctctcagagc gctcatagcc attataagac   2460

ctaaaaaggc agtgctctgc ggggatccca aacagtgcgg tttttttaac atgatgtgcc   2520

tgaaagtgca ttttaaccac gagatttgca cacaagtctt ccacaaaagc atctctcgcc   2580

gttgcactaa atctgtgact tcggtcgtct caaccttgtt ttacgacaaa aaaatgagaa   2640

cgacgaatcc gaaagagact aagattgtga ttgacactac cggcagtacc aaacctaagc   2700

aggacgatct cattctcact tgtttcagag ggtgggtgaa gcagttgcaa atagattaca   2760

aaggcaacga aataatgacg gcagctgcct ctcaagggct gacccgtaaa ggtgtgtatg   2820

ccgttcggta caaggtgaat gaaaatcctc tgtacgcacc cacctcagaa catgtgaacg   2880

tcctactgac ccgcacggag gaccgcatcg tgtggaaaac actagccggc gacccatgga   2940

taaaaacact gactgccaag taccctggga atttcactgc cacgatagag gagtggcaag   3000

cagagcatga tgccatcatg aggcacatct tggagagacc ggaccctacc gacgtcttcc   3060

agaataaggc aaacgtgtgt tgggccaagg ctttagtgcc ggtgctgaag accgctggca   3120

tagacatgac cactgaacaa tggaacactg tggattattt tgaaacggac aaagctcact   3180

cagcagagat agtattgaac caactatgcg tgaggttctt tggactcgat ctggactccg   3240

gtctattttc tgcacccact gttccgttat ccattaggaa taatcactgg gataactccc   3300

cgtcgcctaa catgtacggg ctgaataaag aagtggtccg tcagctctct cgcaggtacc   3360

cacaactgcc tcgggcagtt gccactggaa gagtctatga catgaacact ggtacactgc   3420

gcaattatga tccgcgcata aacctagtac ctgtaaacag aagactgcct catgctttag   3480

tcctccacca taatgaacac ccacagagtg acttttcttc attcgtcagc aaattgaagg   3540

gcagaactgt cctggtggtc ggggaaaagt tgtccgtccc aggcaaaatg gttgactggt   3600

tgtcagaccg gcctgaggct accttcagag ctcggctgga tttaggcatc ccaggtgatg   3660

tgcccaaata tgacataata tttgttaatg tgaggacccc atataaatac catcactatc   3720

agcagtgtga agaccatgcc attaagctta gcatgttgac caagaaagct tgtctgcatc   3780

tgaatcccgg cggaacctgt gtcagcatag gttatggtta cgctgacagg gccagcgaaa   3840

gcatcattgg tgctatagcg cggcagttca agttttcccg ggtatgcaaa ccgaaatcct   3900

cacttgaaga gacggaagtt ctgtttgtat tcattcggta cgatcgcaag gcccgtacgc   3960
```

```
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
```

```
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
```

```
tggtgaaagt aaaagatgct gaagatcagt tgggtgcacg agtgggttac atcgaactgg   8760

atctcaacag cggtaagatc cttgagagtt ttcgccccga agaacgtttt ccaatgatga   8820

gcacttttaa agttctgcta tgtggcgcgg tattatcccg tgttgacgcc gggcaagagc   8880

aactcggtcg ccgcatacac tattctcaga atgacttggt tgagtactca ccagtcacag   8940

aaaagcatct tacggatggc atgacagtaa gagaattatg cagtgctgcc ataaccatga   9000

gtgataacac tgcggccaac ttacttctga caacgatcgg aggaccgaag gagctaaccg   9060

ctttttttgca caacatgggg gatcatgtaa ctcgccttga tcgttgggaa ccggagctga   9120

atgaagccat accaaacgac gagcgtgaca ccacgatgcc tgtagcaatg gcaacaacgt   9180

tgcgcaaact attaactggc gaactactta ctctagcttc ccggcaacaa ttaatagact   9240

ggatggaggc ggataaagtt gcaggaccac ttctgcgctc ggcccttccg gctggctggt   9300

ttattgctga taaatctgga gccggtgagc gtgggtctcg cggtatcatt gcagcactgg   9360

ggccagatgg taagccctcc cgtatcgtag ttatctacac gacggggagt caggcaacta   9420

tggatgaacg aaatagacag atcgctgaga taggtgcctc actgattaag cattggtaac   9480

tgtcagacca agtttactca tatatacttt agattgattt aaaacttcat ttttaattta   9540

aaaggatcta ggtgaagatc ctttttgata atctcatgac caaaatccct taacgtgagt   9600

tttcgttcca ctgagcgtca gaccccgtag aaaagatcaa aggatcttct tgagatcctt   9660

tttttctgcg cgtaatctgc tgcttgcaaa caaaaaaacc accgctacca gcggtggttt   9720

gtttgccgga tcaagagcta ccaactcttt ttccgaaggt aactggcttc agcagagcgc   9780

agataccaaa tactgtcctt ctagtgtagc cgtagttagg ccaccacttc aagaactctg   9840

tagcaccgcc tacatacctc gctctgctaa tcctgttacc agtggctgct gccagtggcg   9900

ataagtcgtg tcttaccggg ttggactcaa gacgatagtt accggataag gcgcagcggt   9960

cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276
```

<210> SEQ ID NO 5
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 5

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480
```

```
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggcgacgaa accgtgttaa     660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
```

-continued

```
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
```

```
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
```

```
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
```

```
cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276
```

<210> SEQ ID NO 6
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 6

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaggcagacg   1620

tcgacttgat gttacaagag gctggggccg gctcagtgga gacacctcgt ggcttgataa   1680
```

```
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatgggg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
```

```
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
```

```
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
```

```
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                  10276
```

<210> SEQ ID NO 7
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 7

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
```

-continued

```
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
```

```
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
```

-continued

```
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
```

```
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
```

```
tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276
```

<210> SEQ ID NO 8
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 8

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa catagggcta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaggcagacg   1620

tcgacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800
```

```
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggbg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
```

```
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
```

```
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
```

```
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                  10276
```

<210> SEQ ID NO 9
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 9

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
```

```
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
```

```
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
```

```
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
```

-continued

```
acccagaccg ccaagctgaa ggtgaccaag ggtggccccc tgcccttcgc ctgggacatc   7800

ctgtcccctc agttcatgta cggctccaag gcctacgtga agcaccccgc cgacatcccc   7860

gactacttga agctgtcctt ccccgagggc ttcaagtggg agcgcgtgat gaacttcgag   7920

gacggcggcg tggtgaccgt gacccaggac tcctccctgc aggacggcga gttcatctac   7980

aaggtgaagc tgcgcggcac caacttcccc tccgacggcc ccgtaatgca gaagaagacc   8040

atgggctggg aggcctcctc cgagcggatg taccccgagg acggcgccct gaagggcgag   8100

atcaagcaga ggctgaagct gaaggacggc ggccactacg acgctgaggt caagaccacc   8160

tacaaggcca agaagcccgt gcagctgccc ggcgcctaca acgtcaacat caagttggac   8220

atcacctccc acaacgagga ctacaccatc gtggaacagt acgaacgcgc cgagggccgc   8280

cactccaccg gcggcatgga cgagctgtac aagtaggaat tggcaagctg cttacataga   8340

actcgcggcg attggcatgc cgccttaaaa tttttatttt atttttcttt tcttttccga   8400

atcggatttt gtttttaata tttcaaaaaa aaaaaaaaaa aaaaaaaaaa cgcgtcgagg   8460

ggaattaatt cttgaagacg aaagggccag gtggcacttt tcggggaaat gtgcgcggaa   8520

cccctatttg tttatttttc taaatacatt caaatatgta tccgctcatg agacaataac   8580

cctgataaat gcttcaataa tattgaaaaa ggaagagtat gagtattcaa catttccgtg   8640

tcgcccttat tccctttttt gcggcatttt gccttcctgt ttttgctcac ccagaaacgc   8700

tggtgaaagt aaaagatgct gaagatcagt tgggtgcacg agtgggttac atcgaactgg   8760

atctcaacag cggtaagatc cttgagagtt ttcgccccga agaacgtttt ccaatgatga   8820

gcacttttaa agttctgcta tgtggcgcgg tattatcccg tgttgacgcc gggcaagagc   8880

aactcggtcg ccgcatacac tattctcaga atgacttggt tgagtactca ccagtcacag   8940

aaaagcatct tacggatggc atgacagtaa gagaattatg cagtgctgcc ataaccatga   9000

gtgataacac tgcggccaac ttacttctga caacgatcgg aggaccgaag gagctaaccg   9060

cttttttgca caacatgggg gatcatgtaa ctcgccttga tcgttgggaa ccggagctga   9120

atgaagccat accaaacgac gagcgtgaca ccacgatgcc tgtagcaatg gcaacaacgt   9180

tgcgcaaact attaactggc gaactactta ctctagcttc ccggcaacaa ttaatagact   9240

ggatggaggc ggataaagtt gcaggaccac ttctgcgctc ggcccttccg gctggctggt   9300

ttattgctga taaatctgga gccggtgagc gtgggtctcg cggtatcatt gcagcactgg   9360

ggccagatgg taagccctcc cgtatcgtag ttatctacac gacggggagt caggcaacta   9420

tggatgaacg aaatagacag atcgctgaga taggtgcctc actgattaag cattggtaac   9480

tgtcagacca agtttactca tatatacttt agattgattt aaaacttcat ttttaattta   9540

aaaggatcta ggtgaagatc ctttttgata atctcatgac caaaatccct taacgtgagt   9600

tttcgttcca ctgagcgtca gaccccgtag aaaagatcaa aggatcttct tgagatcctt   9660

tttttctgcg cgtaatctgc tgcttgcaaa caaaaaaacc accgctacca gcggtggttt   9720

gtttgccgga tcaagagcta ccaactcttt ttccgaaggt aactggcttc agcagagcgc   9780

agataccaaa tactgtcctt ctagtgtagc cgtagttagg ccaccacttc aagaactctg   9840

tagcaccgcc tacatacctc gctctgctaa tcctgttacc agtggctgct gccagtggcg   9900

ataagtcgtg tcttaccggg ttggactcaa gacgatagtt accggataag gcgcagcggt   9960

cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140
```

gaaacgcctg gtatctttat agtcctgtcg ggtttcgcca cctctgactt gagcgtcgat 10200
ttttgtgatg ctcgtcaggg gggcggagcc tatggaaaaa cgccagcaac gcgagctcta 10260
atacgactca ctatag 10276

<210> SEQ ID NO 10
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 10
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860

```
tgccagaggg acatgcaata cccgtccagg actttcaagc tctgagtgaa agtgccacca   1920
ttgtgtacaa cgaacgtgag ttcgtaaaca ggtacctgca ccatattgcc acacatgggg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
```

```
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
```

```
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
```

```
gtgataacac tgcggccaac ttacttctga caacgatcgg aggaccgaag gagctaaccg   9060

cttttttgca caacatgggg gatcatgtaa ctcgccttga tcgttgggaa ccggagctga   9120

atgaagccat accaaacgac gagcgtgaca ccacgatgcc tgtagcaatg gcaacaacgt   9180

tgcgcaaact attaactggc gaactactta ctctagcttc ccggcaacaa ttaatagact   9240

ggatggaggc ggataaagtt gcaggaccac ttctgcgctc ggcccttccg gctggctggt   9300

ttattgctga taaatctgga gccggtgagc gtgggtctcg cggtatcatt gcagcactgg   9360

ggccagatgg taagccctcc cgtatcgtag ttatctacac gacggggagt caggcaacta   9420

tggatgaacg aaatagacag atcgctgaga taggtgcctc actgattaag cattggtaac   9480

tgtcagacca agtttactca tatatacttt agattgattt aaaacttcat ttttaattta   9540

aaaggatcta ggtgaagatc ctttttgata atctcatgac caaaatccct taacgtgagt   9600

tttcgttcca ctgagcgtca gaccccgtag aaaagatcaa aggatcttct tgagatcctt   9660

tttttctgcg cgtaatctgc tgcttgcaaa caaaaaaacc accgctacca gcggtggttt   9720

gtttgccgga tcaagagcta ccaactcttt ttccgaaggt aactggcttc agcagagcgc   9780

agataccaaa tactgtcctt ctagtgtagc cgtagttagg ccaccacttc aagaactctg   9840

tagcaccgcc tacatacctc gctctgctaa tcctgttacc agtggctgct gccagtggcg   9900

ataagtcgtg tcttaccggg ttggactcaa gacgatagtt accggataag gcgcagcggt   9960

cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276
```

```
<210> SEQ ID NO 11
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 11
```

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720
```

```
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
```

```
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
```

```
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
```

```
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
```

ttttgtgatg ctcgtcaggg gggcggagcc tatggaaaaa cgccagcaac gcgagctcta 10260
atacgactca ctatag 10276

<210> SEQ ID NO 12
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 12
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatgggg 1980

```
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
```

```
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
```

```
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
```

```
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                  10276
```

<210> SEQ ID NO 13
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 13

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
```

```
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataaggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
```

```
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
```

```
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
```

```
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                  10276
```

<210> SEQ ID NO 14
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 14
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa catagggcta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaggcagacg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740
ctgtactcaa gagtgaaaaa ttatcttgca tccaccctct cgctgaacaa gtcatagtga 1800
taacacactc tggccgaaaa gggcgttatg ccgtggaacc ataccatggt aaagtagtgg 1860
tgccagaggg acatgcaata cccgtccagg actttcaagc tctgagtgaa agtgccacca 1920
ttgtgtacaa cgaacgtgag ttcgtaaaca ggtacctgca ccatattgcc acacatgggg 1980
gagcgctgaa cactgatgaa gaatattaca aaactgtcaa gcccagcgag cacgacggcg 2040

```
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
```

```
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
```

```
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
```

tgcgcaaact attaactggc gaactactta ctctagcttc ccggcaacaa ttaatagact 9240
ggatggaggc ggataaagtt gcaggaccac ttctgcgctc ggcccttccg gctggctggt 9300
ttattgctga taaatctgga gccggtgagc gtgggtctcg cggtatcatt gcagcactgg 9360
ggccagatgg taagccctcc cgtatcgtag ttatctacac gacggggagt caggcaacta 9420
tggatgaacg aaatagacag atcgctgaga taggtgcctc actgattaag cattggtaac 9480
tgtcagacca agtttactca tatatacttt agattgattt aaaacttcat ttttaattta 9540
aaaggatcta ggtgaagatc ctttttgata atctcatgac caaaatccct taacgtgagt 9600
tttcgttcca ctgagcgtca gaccccgtag aaaagatcaa aggatcttct tgagatcctt 9660
tttttctgcg cgtaatctgc tgcttgcaaa caaaaaaacc accgctacca gcggtggttt 9720
gtttgccgga tcaagagcta ccaactcttt ttccgaaggt aactggcttc agcagagcgc 9780
agataccaaa tactgtcctt ctagtgtagc cgtagttagg ccaccacttc aagaactctg 9840
tagcaccgcc tacatacctc gctctgctaa tcctgttacc agtggctgct gccagtggcg 9900
ataagtcgtg tcttaccggg ttggactcaa gacgatagtt accggataag gcgcagcggt 9960
cgggctgaac ggggggttcg tgcacacagc ccagcttgga gcgaacgacc tacaccgaac 10020
tgagatacct acagcgtgag cattgagaaa gcgccacgct tcccgaaggg agaaaggcgg 10080
acaggtatcc ggtaagcggc agggtcggaa caggagagcg cacgagggag cttccagggg 10140
gaaacgcctg gtatctttat agtcctgtcg ggtttcgcca cctctgactt gagcgtcgat 10200
ttttgtgatg ctcgtcaggg gggcggagcc tatggaaaaa cgccagcaac gcgagctcta 10260
atacgactca ctatag 10276

<210> SEQ ID NO 15
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 15
atgggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct ggccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
```

```
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
```

```
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
ggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
```

```
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
cttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
ggccagatgg taagccctcc cgtatcgtag ttatctacac gacggggagt caggcaacta   9420
tggatgaacg aaatagacag atcgctgaga taggtgcctc actgattaag cattggtaac   9480
tgtcagacca agtttactca tatatacttt agattgattt aaaacttcat ttttaattta   9540
aaaggatcta ggtgaagatc ctttttgata atctcatgac caaaatccct taacgtgagt   9600
tttcgttcca ctgagcgtca gaccccgtag aaaagatcaa aggatcttct tgagatcctt   9660
tttttctgcg cgtaatctgc tgcttgcaaa caaaaaaacc accgctacca gcggtggttt   9720
gtttgccgga tcaagagcta ccaactcttt ttccgaaggt aactggcttc agcagagcgc   9780
agataccaaa tactgtcctt ctagtgtagc cgtagttagg ccaccacttc aagaactctg   9840
tagcaccgcc tacatacctc gctctgctaa tcctgttacc agtggctgct gccagtggcg   9900
ataagtcgtg tcttaccggg ttggactcaa gacgatagtt accggataag gcgcagcggt   9960
cgggctgaac ggggggttcg tgcacacagc ccagcttgga gcgaacgacc tacaccgaac  10020
tgagatacct acagcgtgag cattgagaaa gcgccacgct tcccgaaggg agaaaggcgg  10080
acaggtatcc ggtaagcggc agggtcggaa caggagagcg cacgagggag cttccagggg  10140
gaaacgcctg gtatctttat agtcctgtcg ggtttcgcca cctctgactt gagcgtcgat  10200
ttttgtgatg ctcgtcaggg gggcggagcc tatggaaaaa cgccagcaac gcgagctcta  10260
atacgactca ctatag                                                  10276
```

<210> SEQ ID NO 16

```
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 16

atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatgggg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
```

```
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
```

```
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
```

```
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
```

```
ggatggaggc ggataaagtt gcaggaccac ttctgcgctc ggcccttccg gctggctggt   9300

ttattgctga taaatctgga gccggtgagc gtgggtctcg cggtatcatt gcagcactgg   9360

ggccagatgg taagccctcc cgtatcgtag ttatctacac gacggggagt caggcaacta   9420

tggatgaacg aaatagacag atcgctgaga taggtgcctc actgattaag cattggtaac   9480

tgtcagacca agtttactca tatatacttt agattgattt aaaacttcat ttttaattta   9540

aaaggatcta ggtgaagatc ctttttgata atctcatgac caaaatccct taacgtgagt   9600

tttcgttcca ctgagcgtca gaccccgtag aaaagatcaa aggatcttct tgagatcctt   9660

tttttctgcg cgtaatctgc tgcttgcaaa caaaaaaacc accgctacca gcggtggttt   9720

gtttgccgga tcaagagcta ccaactcttt ttccgaaggt aactggcttc agcagagcgc   9780

agataccaaa tactgtcctt ctagtgtagc cgtagttagg ccaccacttc aagaactctg   9840

tagcaccgcc tacatacctc gctctgctaa tcctgttacc agtggctgct gccagtggcg   9900

ataagtcgtg tcttaccggg ttggactcaa gacgatagtt accggataag gcgcagcggt   9960

cgggctgaac ggggggttcg tgcacacagc ccagcttgga gcgaacgacc tacaccgaac  10020

tgagatacct acagcgtgag cattgagaaa gcgccacgct tcccgaaggg agaaaggcgg  10080

acaggtatcc ggtaagcggc agggtcggaa caggagagcg cacgagggag cttccagggg  10140

gaaacgcctg gtatctttat agtcctgtcg ggtttcgcca cctctgactt gagcgtcgat  10200

ttttgtgatg ctcgtcaggg gggcggagcc tatggaaaaa cgccagcaac gcgagctcta  10260

atacgactca ctatag                                                  10276
```

<210> SEQ ID NO 17
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 17

```
atgggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct ggccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020
```

```
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg tttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
```

-continued

```
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
```

```
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
```

atcaagcaga ggctgaagct gaaggacggc ggccactacg acgctgaggt caagaccacc 8160
tacaaggcca agaagcccgt gcagctgccc ggcgcctaca acgtcaacat caagttggac 8220
atcacctccc acaacgagga ctacaccatc gtggaacagt acgaacgcgc cgagggccgc 8280
cactccaccg gcggcatgga cgagctgtac aagtaggaat tggcaagctg cttacataga 8340
actcgcggcg attggcatgc cgccttaaaa tttttatttt atttttcttt tcttttccga 8400
atcggatttt gtttttaata tttcaaaaaa aaaaaaaaaa aaaaaaaaaa cgcgtcgagg 8460
ggaattaatt cttgaagacg aaagggccag gtggcacttt tcggggaaat gtgcgcggaa 8520
cccctatttg tttatttttc taaatacatt caaatatgta tccgctcatg agacaataac 8580
cctgataaat gcttcaataa tattgaaaaa ggaagagtat gagtattcaa catttccgtg 8640
tcgcccttat tccctttttt gcggcatttt gccttcctgt ttttgctcac ccagaaacgc 8700
tggtgaaagt aaaagatgct gaagatcagt tgggtgcacg agtgggttac atcgaactgg 8760
atctcaacag cggtaagatc cttgagagtt ttcgccccga agaacgtttt ccaatgatga 8820
gcacttttaa agttctgcta tgtggcgcgg tattatcccg tgttgacgcc gggcaagagc 8880
aactcggtcg ccgcatacac tattctcaga atgacttggt tgagtactca ccagtcacag 8940
aaaagcatct tacggatggc atgacagtaa gagaattatg cagtgctgcc ataaccatga 9000
gtgataacac tgcggccaac ttacttctga caacgatcgg aggaccgaag gagctaaccg 9060 ctttttttgca caacatgggg gatcatgtaa ctcgccttga tcgttgggaa ccggagctga 9120
atgaagccat accaaacgac gagcgtgaca ccacgatgcc tgtagcaatg gcaacaacgt 9180
tgcgcaaact attaactggc gaactactta ctctagcttc ccggcaacaa ttaatagact 9240
ggatggaggc ggataaagtt gcaggaccac ttctgcgctc ggcccttccg gctggctggt 9300
ttattgctga taaatctgga gccggtgagc gtgggtctcg cggtatcatt gcagcactgg 9360
ggccagatgg taagccctcc cgtatcgtag ttatctacac gacggggagt caggcaacta 9420
tggatgaacg aaatagacag atcgctgaga taggtgcctc actgattaag cattggtaac 9480
tgtcagacca agtttactca tatatacttt agattgattt aaaacttcat ttttaattta 9540
aaaggatcta ggtgaagatc ctttttgata atctcatgac caaaatccct taacgtgagt 9600
tttcgttcca ctgagcgtca gaccccgtag aaaagatcaa aggatcttct tgagatcctt 9660
tttttctgcg cgtaatctgc tgcttgcaaa caaaaaaacc accgctacca gcggtggttt 9720
gtttgccgga tcaagagcta ccaactcttt ttccgaaggt aactggcttc agcagagcgc 9780
agataccaaa tactgtcctt ctagtgtagc cgtagttagg ccaccacttc aagaactctg 9840
tagcaccgcc tacatacctc gctctgctaa tcctgttacc agtggctgct gccagtggcg 9900
ataagtcgtg tcttaccggg ttggactcaa gacgatagtt accggataag gcgcagcggt 9960
cgggctgaac ggggggttcg tgcacacagc ccagcttgga gcgaacgacc tacaccgaac 10020
tgagatacct acagcgtgag cattgagaaa gcgccacgct tcccgaaggg agaaaggcgg 10080
acaggtatcc ggtaagcggc agggtcggaa caggagagcg cacgagggag cttccagggg 10140
gaaacgcctg gtatctttat agtcctgtcg ggtttcgcca cctctgactt gagcgtcgat 10200
ttttgtgatg ctcgtcaggg gggcggagcc tatggaaaaa cgccagcaac gcgagctcta 10260
atacgactca ctatag 10276

<210> SEQ ID NO 18
<211> LENGTH: 10276
<212> TYPE: DNA
<213> ORGANISM: Artificial Sequence
<220> FEATURE:
<223> OTHER INFORMATION: Synthetic Polynucleotide

<400> SEQUENCE: 18

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatgggg   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
```

```
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaattctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct gagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

```
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagattcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtatgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
```

```
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg attgaattgg ccaccatggt gagcaagggc   7620
gaggaggata acatggccat catcaaggag ttcatgcgct tcaaggtgca catggagggc   7680
tccgtgaacg gccacgagtt cgagatcgag ggcgagggcg agggccgccc ctacgagggc   7740
acccagaccg ccaagctgaa ggtgaccaag ggtggccccc tgcccttcgc ctgggacatc   7800
ctgtcccctc agttcatgta cggctccaag gcctacgtga agcaccccgc cgacatcccc   7860
gactacttga agctgtcctt ccccgagggc ttcaagtggg agcgcgtgat gaacttcgag   7920
gacggcggcg tggtgaccgt gacccaggac tcctccctgc aggacggcga gttcatctac   7980
aaggtgaagc tgcgcggcac caacttcccc tccgacggcc ccgtaatgca gaagaagacc   8040
atgggctggg aggcctcctc cgagcggatg taccccgagg acggcgccct gaagggcgag   8100
atcaagcaga ggctgaagct gaaggacggc ggccactacg acgctgaggt caagaccacc   8160
tacaaggcca agaagcccgt gcagctgccc ggcgcctaca acgtcaacat caagttggac   8220
atcacctccc acaacgagga ctacaccatc gtggaacagt acgaacgcgc cgagggccgc   8280
cactccaccg gcggcatgga cgagctgtac aagtaggaat tggcaagctg cttacataga   8340
actcgcggcg attggcatgc cgccttaaaa tttttatttt atttttcttt tcttttccga   8400
atcggatttt gtttttaata tttcaaaaaa aaaaaaaaaa aaaaaaaaaa cgcgtcgagg   8460
ggaattaatt cttgaagacg aaagggccag gtggcacttt tcggggaaat gtgcgcggaa   8520
cccctatttg tttatttttc taaatacatt caaatatgta tccgctcatg agacaataac   8580
cctgataaat gcttcaataa tattgaaaaa ggaagagtat gagtattcaa catttccgtg   8640
tcgcccttat tccctttttt gcggcatttt gccttcctgt ttttgctcac ccagaaacgc   8700
tggtgaaagt aaaagatgct gaagatcagt tgggtgcacg agtgggttac atcgaactgg   8760
atctcaacag cggtaagatc cttgagagtt ttcgccccga agaacgtttt ccaatgatga   8820
gcacttttaa agttctgcta tgtggcgcgg tattatcccg tgttgacgcc gggcaagagc   8880
aactcggtcg ccgcatacac tattctcaga atgacttggt tgagtactca ccagtcacag   8940
aaaagcatct tacggatggc atgacagtaa gagaattatg cagtgctgcc ataaccatga   9000
gtgataacac tgcggccaac ttacttctga caacgatcgg aggaccgaag gagctaaccg   9060
ctttttttgca caacatgggg gatcatgtaa ctcgccttga tcgttgggaa ccggagctga   9120
atgaagccat accaaacgac gagcgtgaca ccacgatgcc tgtagcaatg gcaacaacgt   9180
tgcgcaaact attaactggc gaactactta ctctagcttc ccggcaacaa ttaatagact   9240
ggatggaggc ggataaagtt gcaggaccac ttctgcgctc ggcccttccg gctggctggt   9300
ttattgctga taaatctgga gccggtgagc gtgggtctcg cggtatcatt gcagcactgg   9360
```

ggccagatgg taagccctcc cgtatcgtag ttatctacac gacggggagt caggcaacta 9420
tggatgaacg aaatagacag atcgctgaga taggtgcctc actgattaag cattggtaac 9480
tgtcagacca agtttactca tatatacttt agattgattt aaaacttcat ttttaattta 9540
aaaggatcta ggtgaagatc ctttttgata atctcatgac caaaatccct taacgtgagt 9600
tttcgttcca ctgagcgtca gaccccgtag aaaagatcaa aggatcttct tgagatcctt 9660
tttttctgcg cgtaatctgc tgcttgcaaa caaaaaaacc accgctacca gcggtggttt 9720
gtttgccgga tcaagagcta ccaactcttt ttccgaaggt aactggcttc agcagagcgc 9780
agataccaaa tactgtcctt ctagtgtagc cgtagttagg ccaccacttc aagaactctg 9840
tagcaccgcc tacatacctc gctctgctaa tcctgttacc agtggctgct gccagtggcg 9900
ataagtcgtg tcttaccggg ttggactcaa gacgatagtt accggataag gcgcagcggt 9960
cgggctgaac ggggggttcg tgcacacagc ccagcttgga gcgaacgacc tacaccgaac 10020
tgagatacct acagcgtgag cattgagaaa gcgccacgct tcccgaaggg agaaaggcgg 10080
acaggtatcc ggtaagcggc agggtcggaa caggagagcg cacgagggag cttccagggg 10140
gaaacgcctg gtatctttat agtcctgtcg ggtttcgcca cctctgactt gagcgtcgat 10200
ttttgtgatg ctcgtcaggg gggcggagcc tatggaaaaa cgccagcaac gcgagctcta 10260
atacgactca ctatag 10276

<210> SEQ ID NO 19
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 19
atgggcgcgc cctcagcatc gattgaattg gccaccatgg tgagcaaggg cgagga 56

<210> SEQ ID NO 20
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 20
tcgccgcgag ttctatgtaa gcagcttgcc aattcctact tgtacagctc gtcca 55

<210> SEQ ID NO 21
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 21
aaataaaata aaaattttaa ggcggcatgc caatcgccgc gagttctatg taa 53

<210> SEQ ID NO 22
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 22
tattgggcgc tcttccgctg gtctcacacc atgggcggcg catgagagaa 50

<210> SEQ ID NO 23
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 23
tcagtgagcg aggaagcggt ctcattatac gactatacgc tggttgag 48

<210> SEQ ID NO 24
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 24
tattgggcgc tcttccgctg gtctcacacc tggcaacaga tgtcagtgcg 50

<210> SEQ ID NO 25
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 25
tcagtgagcg aggaagcggt ctcattataa tgatgccaga cttgcctg 48

<210> SEQ ID NO 26
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 26
tattgggcgc tcttccgctg gtctcacacc taccaagtac caaccatagg 50

<210> SEQ ID NO 27
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 27
tcagtgagcg aggaagcggt ctcattattt cagcccgtac atgttagg 48

<210> SEQ ID NO 28
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 28
tattgggcgc tcttccgctg gtctcacacc taatcactgg gataactccc 50

<210> SEQ ID NO 29
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 29
tcagtgagcg aggaagcggt ctcattatca tctgcatcag tggtgtct 48

<210> SEQ ID NO 30
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 30
tattgggcgc tcttccgctg gtctcacacc ttgaaccatt tgctgacagc 50

<210> SEQ ID NO 31
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 31
tcagtgagcg aggaagcggt ctcattattc ctctctagtg atcaccct 48

<210> SEQ ID NO 32
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 32
tattgggcgc tcttccgctg gtctcacacc agaaccagcc tagtttccac 50

<210> SEQ ID NO 33
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 33
tcagtgagcg aggaagcggt ctcattataa ccagctctcg gtggattc 48

<210> SEQ ID NO 34
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 34
tattgggcgc tcttccgctg gtctcacacc gctagcaaca gcgtatctgt 50

<210> SEQ ID NO 35
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 35
tcagtgagcg aggaagcggt ctcattatat ggccatgtta tcctcctc 48

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
gcgcggctgt tcaagttttc 20

<210> SEQ ID NO 37
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 37
tttcccattt cttgtccctg cagtatatgg ctacatctgc atcagtggtg tct 53

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
atgcagatgt agccatatac 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
gatcacccta ttcacgcctg 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 40
caggcgtgaa tagggtgatc 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
cttctgcctt caaataatgc 20

<210> SEQ ID NO 42
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 42
tattgggcgc tcttccgctg gtctcacacc agcataggtt atggttacgc 50

<210> SEQ ID NO 43
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 43
tcagtgagcg aggaagcggt ctcattatta cgcaggcact ttcggtga 48

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
atgccgtagg accaaacttc 20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
tggtgtctaa agctgtcagc 20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
cttcaaggtg cacatggagg 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
aggacagctt caagtagtcg 20

<210> SEQ ID NO 48
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 48
caccattggc aatgagcggt tc 22

<210> SEQ ID NO 49

```
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 49

aggtctttgc ggatgtccac gt                                              22


<210> SEQ ID NO 50
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 50

gcggcatgtt ctggatttga ctc                                             23


<210> SEQ ID NO 51
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 51

ccaccacagt tgctgactca tc                                              22
```